(12) United States Patent
Bout et al.

(10) Patent No.: US 10,562,956 B2
(45) Date of Patent: Feb. 18, 2020

(54) RECOMBINANT FIBRINOGEN

(71) Applicant: Mallinckrodt Pharma IP Trading D.A.C., an Irish Designated Activity Company, Dublin (IE)

(72) Inventors: Abraham Bout, Moerkapelle (NL); Joseph Grimbergen, Lisse (NL); Jacob Koopman, Leiderdorp (NL)

(73) Assignee: Mallinckrodt Pharma IP Trading D.A.C., Dublin (IE)

( * ) Notice: Subject to any disclaimer, the term of this patent is extended or adjusted under 35 U.S.C. 154(b) by 179 days.

(21) Appl. No.: 15/331,942

(22) Filed: Oct. 24, 2016

(65) Prior Publication Data
US 2017/0037108 A1 Feb. 9, 2017

Related U.S. Application Data

(63) Continuation of application No. 13/002,797, filed as application No. PCT/EP2009/058754 on Jul. 9, 2019, now abandoned.

(30) Foreign Application Priority Data

Jul. 9, 2008 (EP) .................................... 08159999

(51) Int. Cl.
*C07K 14/75* (2006.01)
*C07H 21/04* (2006.01)
*C12N 15/09* (2006.01)

(52) U.S. Cl.
CPC .................................. *C07K 14/75* (2013.01)

(58) Field of Classification Search
None
See application file for complete search history.

(56) References Cited

U.S. PATENT DOCUMENTS

| | | | |
|---|---|---|---|
| 6,037,457 | A | 3/2000 | Lord |
| 2003/0221223 | A1 | 11/2003 | Huang et al. |

FOREIGN PATENT DOCUMENTS

| | | |
|---|---|---|
| EP | 0992586 | 4/2000 |
| EP | 1661989 | 5/2006 |
| WO | 2000077227 A1 | 12/2000 |
| WO | 2003087160 A1 | 10/2003 |
| WO | 2005116235 A2 | 12/2005 |
| WO | 199523868 A1 | 5/2006 |
| WO | 2006122822 | 11/2006 |
| WO | 2006125021 A2 | 11/2006 |
| WO | 2007103447 | 9/2007 |
| WO | 2007103447 A2 | 9/2007 |

OTHER PUBLICATIONS

Welch, M., et al. 2009 J.R. Soc. Interface 6: 5467-5476. (Year: 2009).*

Coco-Martin M. J. and Harmsen M. M., A Review of Therapeutic Protein Expression by Mammalian Cells, BioProcess International, Jun. 2008, Supplement Chapter 4, 4 pages.
European Application No. 09793957.3 Notice of Opposition and Statement of Facts dated Feb. 10, 2017, 28 pages.
European Application No. 16168954.2, Examination Report dated Dec. 20, 2017, 6 pages.
Evaluation of cDNA sequences optimized for high level stable expression of recombinant rhFibrinogen in CHO cells using transient transfections experiments in a CHO-S cell line, Author Unknown, Publication Unknown, Date Unknown, 6 pages.
Geneart GMBH presentation: Genomics and Bioinformatics in Medicine Workshop, 2006, 37 pages.
Gorkun O., et al., The Conversion of Fibrinogen to Fibrin: Recombinant Fibrinogen Typifies Plasma Fibrinogen, Blood Journal, 1997, pp. 4407-4414, vol. 89, No. 12.
Gustafsson C., et al., Codon Bias and Heterologous Protein Expression, Trends in Biotechnology, 2004, pp. 346-353, vol. 22, No. 7.
Lonza Biologics, Cell Line Development and Engineering Workshop, Prague, Mar. 2008, 48 pages.
Rooney M.M., et al., The Contribution of the Three Hypothesized Integrin-Binding Sites in Fibrinogen to Platelet-Mediated Clot Retraction, Blood 1998, pp. 2374-2381, vol. 92, No. 7.
Roy, S.N., et al., Assembly and Secretion of Recombinant Human Fibrinogen, The Journal of Biological Chemistry, 1991, pp. 4758-4763, vol. 266, No. 8.
Canadian Application No. 2,730,030, Office action dated Nov. 8, 2016, 3 pages.
Canadian Application No. 2,730,030, Office action dated Aug. 28, 2017, 4 pages.
European Application No. 16168954.2, Partial Search Report dated Sep. 2, 2016, 8 pages.
European Application No. 16168954.2, Extended Search Report dated Jan. 23, 2017, 17 pages.
European Application No. 16168954.2, Communication pursuant To Rule 114(2) EPC dated Oct. 27, 2017, 6 pages.
Hoegee-De Nobel, E., et al, A monoclonal antibody-based quantitative enzyme immunoassay for the determination of plasma fibrinogen concentrations, 1988, Thromb. Haemost., pp. 415-418, vol. 60, No. 3.
Koch, C. et al., Anti-Hirudin Monoclonal Antibodies Directed Toward Discontinuous Epitopes Of The Hirudin Amino-Terminal And Epitopes Involving The Carboxy-Terminal Hirudin Amino Acids, 1993, Analytical Biochem., pp. 301-312, vol. 214, No. 1.
Koopman, J. et al., Fibrinogen Marburg: a homozygous case of dysfibrinogenemia, lacking amino acids A alpha 461-610 (Lys 461 AAA- >stop TAA)., 1992, Blood, pp. 1972-1979, vol. 80, No. 8.
Koppert, P.W., Huijsmans, C.M. and Nieuwenhuizen, W., A monoclonal antibody, specific for human fibrinogen, fibrinopeptide A-containing fragments and not reacting with free fibrinopeptide A, 1985, Blood, pp. 503-507, vol. No. 3.
Zaidi, et al, M.; "Development and Performance of a Highly Sensitive and Specific Two-Site Immunometric Assay Of Calcitonin Gene-Related Peptide"; 1990, Clin. Chem., pp. 1288-1294, vol. 36, No. 7.
PCT/EP2009/058754, International Search Report dated Jan. 9, 2009, 3 pages.

* cited by examiner

*Primary Examiner* — Marsha Tsay

(57) ABSTRACT

The present invention relates to nucleotide sequences encoding a fibrinogen alpha, beta or gamma chain. The sequences are optimized for expression in a eukaryotic cell culture system. Such optimized nucleotide sequences allow for the efficient expression of recombinant fibrinogen and variants thereof in intact form in a eukaryotic cell culture system.

8 Claims, 6 Drawing Sheets

Specification includes a Sequence Listing.

RECOMBINANT FIBRINOGEN

CROSS REFERENCE TO RELATED APPLICATION

This application is a continuation application of U.S. application Ser. No. 13/002,797, filed on Apr. 8, 2011, which is a National Stage Entry of PCT/EP2009/058754, filed on Jul. 9, 2009 and claims benefit to EP Patent Application No. 08159999.5, filed on Jul. 9, 2008, each of which are herein incorporated by reference in its entirety.

TECHNICAL FIELD

The present invention relates to recombinant fibrinogen, to methods for producing it at high levels in mammalian cells and to its applications.

BACKGROUND ART

Fibrinogen is a soluble plasma glycoprotein which is synthesized in the human body primarily by liver parenchymal cells. It is a dimeric molecule, consisting of two pairs of three polypeptide chains designated A.alpha., B.beta. and .gamma., which are connected by disulfide bridges. The three polypeptide chains are encoded by three separate genes. The wild-type A.alpha. chain is synthesized as a 625 amino acid precursor and is present in plasma as a 610 amino acids protein, the B.beta. contains 461 and the .gamma. chain 411 amino acids. The three polypeptides are synthesized individually from 3 mRNAs. Assembly of the three component chains (A.alpha., B.beta., and .gamma.) into its final form as a six-chain dimer (A.alpha., B.beta., .gamma.)2 occurs in the lumen of the endoplasmic reticulum (ER).

Fibrinogen circulates in blood at high concentrations (1-2 g/L) and demonstrates a high degree of heterogeneity. Variations arise through genetic polymorphisms, differences in glycosylation and phosphorylations, (partial) proteolysis of the carboxy-terminal part of the A.alpha. chain and alternative splicing (for review see De Maat and Verschuur (2005) Curr. Opin. Hematol. 12, 377; Laurens et al. (2006) J. Thromb Haemost. 4, 932; Henschen-Edman (2001) Ann. N.Y. Acad. Sci. USA 936, 580). It is estimated that in each individual about one million different fibrinogen molecules circulate. Most of these variants, which account for just a small portion of the total fibrinogen (in most cases not more than a few percents), differ in function and structure. Proteolysis of the carboxy-terminal part of the A.alpha. chain results in three major circulating forms of fibrinogen having clearly different molecular weights. Fibrinogen is synthesized in the high-molecular weight form (HMW; molecular weight 340 kDa; the predominant form of A.alpha. chains in the circulation contains 610 amino acids). The degradation of one of the A.alpha. chains gives the low-molecular weight form (LMW; MW=305 kDa); the LMW' form (270 kDa) is the variant where both A.alpha. chains are partially degraded at the carboxy-terminus. In normal blood, 50-70% of the fibrinogen is HMW, 20-50% is fibrinogen with one or two degraded A.alpha. chains (de Maat and Verschuur (2005) Curr. Opin. Hematol. 12, 377). The HMW and LMW' variants show distinct differences in clotting time and fibrin polymer structure (Hasegawa N, Sasaki S. (1990) Thromb. Res. 57, 183).

Well-known variants which are the result of alternative splicing are the so-called .gamma.' variant and the Fib420 variant.

The .gamma.' variant represents about 8% of the total of .gamma.-chains. It consists of 427 amino acids rather than 411 for the most abundant .gamma.-chain; the four C-terminal amino acids (AGDV) are replaced by 20 amino acids that contain 2 sulphated tyrosines. The fibrinogen .gamma.' chain is not able to bind to the platelet fibrinogen receptor IIb.beta.3, which is critical in regulating platelet aggregation.

The Fib420 variant, which has a molecular weight of 420 kDa, accounts for 1-3% of the total circulating fibrinogen (de Maat and Verschuur (2005) Curr. Opin. Hematol. 12, 377). Through alternative splicing, an extra open reading frame is included at the C-terminus of the A.alpha.-chain, thereby extending it with 237 amino acids. The additional amino acids form a nodular structure.

Plasma derived fibrinogen is an important component of marketed fibrin sealants which are clinically applied during surgical interventions to stop bleeding and to decrease blood and fluid loss. In addition it is used to facilitate tissue adherence by using the agglutination property of fibrin and to improve wound healing. Fibrinogen is also used clinically to supplement fibrinogen deficiency in hereditary fibrinogenemia patients and in patients with an acquired fibrinogen deficiency. Intravenous administration of high dosage of fibrinogen (3-10 gram) has demonstrated to normalize clotting of blood and arrest or prevent serious bleeding in various clinical situations.

Recombinant production of human fibrinogen, be it in wild-type (HMW) format or as a variant (e.g as Fib420), has many advantages over the use of plasma derived materials. These include its preferred safety profile, the possibility to make variants in a pure way and unlimited supply. However, in order to produce it in an economically feasible way, high expression levels of intact, functional fibrinogen are required. In addition, for specific applications (e.g. use of fibrinogen as an intravenous (IV) hemostat) proper post-translational modifications (e.g. glycosylation) are required.

Because of the post-translational modifications, expression in mammalian systems is preferred. Therefore, biologically active recombinant fibrinogen has been expressed in various cells, such as baby hamster kidney (BHK) (e.g. Farrell et al. (1991) Biochemistry 30, 9414), Chinese Hamster Ovary (CHO) cells (e.g. Lord, (U.S. Pat. No. 6,037, 457), Binnie et al. (1993) Biochemistry 32, 107), or African Green Monkey derived COS cells (e.g. Roy et al. (1991) J. Biol. Chem. 266, 4758). However, the expression levels are only around 1-15 .mu.g/ml and considered inadequate to replace the large amounts of plasma fibrinogen needed in clinical practice. In addition, expression of human fibrinogen in yeast P. pastoris yielded 8 .mu.g/ml, which is also not adequate for commercial manufacturing (Tojo et al. (2008) Prot. Expr. and Purif. 59, 289).

In EP 1 661 989 it is reported that yields of at least 100 mg/L are needed for commercial viable production. In this application levels of up to 631.5 mg/L by CHO cells in a spinner flask are reported. However, in order to reach such levels, cells have to co-express the baculovirus P35 anti-apoptosis protein, and methotrexate, an anti-metabolite, has to be used for amplification of the vectors. Cell densities are relatively low (maximum in spinner flask $9.4 \times 10^5$ cells/ml in 15 days) as compared to what is standard in the industry e.g. Wurm (Nature Biotechnol. (2004) 22, 1393) reports routine cell densities of $2 \times 10^6$ cells/ml in 3-4 days of subcultivation).

The most important issue for the successful production of recombinant fibrinogen is how to make enough intact, properly assembled, biologically active product at high purity.

DETAILED DESCRIPTION OF THE INVENTION

The present invention relates to a nucleotide sequence encoding a fibrinogen alpha, beta or gamma chain which is optimized for expression in a eukaryotic cell culture system. An optimized nucleotide sequence according to the invention allows for the efficient expression of recombinant fibrinogen in intact form in a eukaryotic cell culture system. The protein sequence encoded by the optimized nucleotide sequence is identical to the protein sequence encoded by the corresponding non-optimized nucleotide sequence.

In the context of the present invention, the term 'fibrinogen' may refer to any of the forms of fibrinogen and includes variants which have arisen through genetic polymorphisms, differences in glycosylation and phosphorylations, (partial) proteolysis of the carboxy-terminal part of the A.alpha. chain and alternative splicing. In the context of the present invention, the terms 'alpha chain' and 'A.alpha. chain' are used interchangeably. They may refer to both wild type and variants of the alpha chain, including a fibrinogen alpha chain of 644 amino acids containing a signal sequence (SEQ ID No. 8), a precursor fibrinogen alpha chain of 625 amino acids without signal sequence (amino acids 20 to 644 of SEQ ID NO. 8), a truncated fibrinogen alpha chain of 610 amino acids (amino acids 20 to 629 of SEQ ID NO. 8) as found in circulation and a Fib420 variant alpha chain of 866 amino acids containing a signal sequence (SEQ ID NO. 11) or without a signal sequence (amino acids 20-866 of SEQ ID NO. 11).

In the context of the present invention, the terms 'beta chain' and 'B.beta. chain' are used interchangeably. They may refer to both wild type and variants of the beta chain, including a fibrinogen beta chain of 491 amino acids containing a signal sequence (SEQ ID No. 9) and a fibrinogen beta chain of 461 amino acids without signal sequence (amino acids 31 to 491 of SEQ ID NO. 9).

In the context of the present invention, the term 'gamma chain' and '.gamma. chain' are used interchangeably. They may refer to both wild type and variants of the gamma chain, including a fibrinogen gamma chain of 437 amino acids containing a signal sequence (SEQ ID No. 10), a fibrinogen gamma chain of 411 amino acids without signal sequence (amino acids 27 to 437 of SEQ ID NO. 10), a fibrinogen gamma chain of 453 amino acids, which is the gamma-prime chain with signal sequence (SEQ ID No. 13) and a fibrinogen gamma chain of 427 amino acids, which is the gamma-prime chain without signal sequence (amino acids 27 to 453 of SEQ ID NO. 13).

In the context of the present invention, fibrinogen or a fibrinogen chain is 'in intact form' when the amino acid sequence contains all the amino acids which were encoded for by the nucleotide sequence, optionally without the amino acids which are removed during normal cell (secretion) processing. Therefore, alpha chains having 644, 625 or 610 amino acids are examples of an alpha chain in intact form.

The optimized nucleotide sequences according to the invention have a GC content of at least 55%, preferably of at least 58%, more preferably of at least 60 or 65%. In one embodiment, the optimized nucleotide sequences according to the invention have a GC content in the range of about 55 to 70%. In another embodiment, the optimized nucleotide sequences according to the invention have a GC content in the range of about 60 to 65%.

The optimized nucleotide sequences of the invention encoding a fibrinogen alpha, beta and gamma chain are optimized for expression in a eukaryotic cell culture system. Preferably, they are optimized for expression in a mammalian cell culture system, such as for expression in a COS cell, BHK cell, NS0 cell, Sp2/0 cell, CHO cell, a PER.C6 cell, a HEK293 cell or insect cell culture system. More preferably, the nucleotide sequences are optimized for expression in a human cell culture system, such as for a PER.C6 cell or a HEK293 cell culture system.

The optimization according to the invention has a codon adaptation index of at least 0.90, preferably of at least 0.95, more preferably of at least 0.97. In one embodiment, a nucleotide sequence according to the invention is optimized by codon usage adaptation to CHO cells with a codon adaption index of at least 0.95.

Nucleotide sequences according to the invention may be encoding any type of fibrinogen chains. Preferably they are encoding mammalian fibrinogen chains, more preferably they are encoding primate fibrinogen chains, most preferably they are encoding human fibrinogen chains. Also combinations are possible, such as for example one or two mammalian fibrinogen chains combined with two or one rodent fibrinogen chains. The nucleotide sequence which is optimized may be DNA or RNA. Preferably, it is cDNA.

An optimized nucleotide sequence according to the invention encoding a fibrinogen alpha, beta or gamma chain shows at least 70% identity to its respective non-optimized counterpart. In one embodiment, an optimized nucleotide sequence of the invention encoding a fibrinogen alpha, beta and gamma chain shows 70-80% identity to its respective non-optimized sequences. Preferably, the optimized nucleotide sequences of the invention encoding a fibrinogen alpha, beta or gamma chain contain no cis-acting sites, such as splice sites and poly(A) signals.

An optimized nucleotide sequence according to the invention which encodes a fibrinogen alpha chain contains no 39 basepair direct repeat sequences which are normally present in the gene encoding the alpha chain of human fibrinogen. In an optimized nucleotide sequence according to the invention which encodes an alpha chain, the repeating sequence is changed without changing the encoded protein sequence.

In a preferred embodiment, an optimized nucleotide sequence according to the invention which encodes an alpha chain comprises a sequence according to SEQ ID No. 4 or 7. Nucleotide sequences which encode a fibrinogen alpha chain and which comprise part of these sequences are also encompassed by the present invention. In one embodiment, an optimized nucleotide sequence according to the invention comprises nucleotides 60-1932 of SEQ ID NO. 4. In another embodiment, an optimized nucleotide sequence according to the invention comprises nucleotides 60-1887 of SEQ ID NO. 4. In yet another embodiment, an optimized nucleotide sequence according to the invention comprises nucleotides 60-2598 of SEQ ID NO. 7. Also a nucleotide sequence which comprises a sequence which is at least 85%, at least 87% or at least 90%, more preferably at least 92%, at least 94%, 96%, most preferably at least 98% or at least 99% identical to SEQ ID NO. 4 or 7 and which encode a fibrinogen alpha chain, for example a fibrinogen alpha chain with a sequence according to SEQ ID NO. 8 or 11 or part of these sequences, such as for example as exemplified above, are encompassed by the present invention.

In a preferred embodiment, an optimized nucleotide sequence according to the invention which encodes a beta chain comprises a sequence according to SEQ ID No. 5. Nucleotide sequences which encode a fibrinogen beta chain and which comprise part of this sequence are also encompassed by the present invention. In one embodiment, an optimized nucleotide sequence according to the invention comprises nucleotides 93-1473 of SEQ ID NO. 5. Also a nucleotide sequence which comprises a sequence which is at least 85%, at least 87% or at least 90%, more preferably at least 92%, at least 94%, 96%, most preferably at least 98% or at least 99% identical to SEQ ID No. 5 and which encodes a fibrinogen beta chain, for example a fibrinogen beta chain with a sequence according to SEQ ID NO. 9 or part of this sequence, such as for example amino acids 31 to 491 of SEQ ID NO. 9, are encompassed by the present invention.

In a preferred embodiment, an optimized nucleotide sequence according to the invention which encodes a fibrinogen gamma chain comprises a sequence according to SEQ ID No. 6. Nucleotide sequences which encode a fibrinogen gamma chain and which comprise part of this sequence are also encompassed by the present invention. In one embodiment, an optimized nucleotide sequence according to the invention which encodes a fibrinogen gamma chain comprises nucleotides 81-1311 of SEQ ID NO. 6. Also a nucleotide sequence which comprises a sequence which is at least 85%, at least 87% or at least 90%, more preferably at least 92%, at least 94%, 96%, most preferably at least 98% or at least 99% identical to SEQ ID No. 6 and which encodes a fibrinogen gamma chain, for example a fibrinogen gamma chain with a sequence according to SEQ ID NO. 10 or part of this sequence, such as for example amino acids 27 to 437 of SEQ ID NO. 10, are encompassed by the present invention.

In another preferred embodiment, an optimized nucleotide sequence according to the invention which encodes a fibrinogen gamma chain comprises a sequence according to SEQ ID No. 12. Nucleotide sequences which encode a fibrinogen gamma chain and which comprise part of this sequence are also encompassed by the present invention. In one embodiment, an optimized nucleotide sequence according to the invention which encodes a fibrinogen gamma chain comprises nucleotides 81-1359 of SEQ ID NO. 12. Also a nucleotide sequence which comprises a sequence which is at least 85%, at least 87% or at least 90%, more preferably at least 92%, at least 94%, 96%, most preferably at least 98% or at least 99% identical to SEQ ID No. 12 and which encodes a fibrinogen gamma chain, for example a fibrinogen gamma chain with a sequence according to SEQ ID NO. 13 or part of this sequence, such as for example amino acids 27 to 453 of SEQ ID NO. 13 are encompassed by the present invention.

In another aspect, the present invention relates to a nucleotide construct which comprises an optimized nucleotide sequence according to the invention which encodes a fibrinogen alpha, beta or gamma chain. The nucleotide construct may comprise regulatory sequences which influence the expression of the fibrinogen chains, including promoters, terminators and enhancers. In one embodiment, the nucleotide construct is a vector, such as for example a cloning vector or expression vector. The nucleotide construct may also comprise a selection marker.

In another aspect, the present invention relates to a cell comprising an optimized nucleotide sequence according to the invention encoding a fibrinogen alpha, beta or gamma chain. In the cell, the nucleotides according to the invention may be present as such or in a construct, such as in an expression vector or a cloning vector. The cell is typically a host cell which is used for the production of fibrinogen. The cell comprising the nucleotide sequence according to the invention is preferably a mammalian cell. Suitable examples of mammalian cells include insect cells, COS cells, BHK cells, NS0 cells, Sp2/0 cells, CHO cells, PER.C6 cells and HEK293 cells.

Cells according to the invention produce high amounts of intact, biologically active fibrinogen. The cell is typically part of a cell line. In the present context, the phrase 'a cell or cell line producing high amounts of intact fibrinogen' refers to a cell or cell line which produces more than 85%, preferably more than 90%, 95% or 99% of intact products. Preferably, this is measured over a period of 10, 20 or 30, more preferably over 40 or 50, population doublings. In the context of the present invention, 'biologically active' fibrinogen refers to fibrinogen which polymerizes into fibrin in the presence of thrombin. Such cells or cell lines are also encompassed by the present invention. In a preferred embodiment, a cell line according to the invention produces intact recombinant fibrinogen at levels of at least 3 picogram per cell per day, more preferably at least 4 or 5 picogram per cell per day, even more preferably at least 7 or 10 picogram per cell per day. In a reactor with a cell density of 30.times.10.sup.6 cell/ml, 3 picogram per cell per day corresponds to 90 mg fibrinogen per liter reactor volume per day, 5 picogram per cell per day corresponds to 150 mg fibrinogen per liter per day and 7 picogram per cell per day corresponds to 210 mg fibrinogen per liter per day. Preferably at least 50% of the cell population, more preferably at least 60%, 70% or 80% of the cell population, most preferably at least 90%, 95% or 99% of the cell population produces at least 3 picogram per cell per day, more preferably at least 5 picogram per cell per day, even more preferably at least 7 picogram per cell per day.

The selection of cells or cell lines which produce high amounts of intact fibrinogen is preferably carried out without the expression of protease inhibitors. In one embodiment, the selection is performed using antibodies, preferably monoclonal antibodies which bind to the intact N-terminus of the alpha chain and intact C-terminus of the alpha chain. Suitable commercially available examples of such antibodies include the Y18 antibody described by Koppert et al. (1985) Blood 66, 503 and the G8 antibody described by Hoegee-de Nobel et al. (1988) Thromb. Haemost. 60(3) 415. Preferably, this selection is performed in a serum-free environment. This method for the selection of cell lines which produce intact fibrinogen is also part of the present invention.

In another aspect, the present invention relates to a method for producing fibrinogen in a eukaryotic cell culture system. The method comprises culturing a host cell or cell line according to the invention under conditions wherein fibrinogen is produced. Optionally, the fibrinogen produced is recovered. Optimized and non-optimized chains may be combined. The non-optimized chains may be obtained by genetic engineering or by synthesis, and they may be from a different source than the optimized chains. In one embodiment, only one chain per fibrinogen molecule is encoded by a codon optimized nucleotide sequence according to the invention, while the two other chains are encoded by two nucleotide sequences which are not optimized. In another embodiment, two of the three fibrinogen chains per fibrinogen molecule are encoded by codon optimized nucleotide sequences according to the invention. In a preferred embodiment, all three fibrinogen chains are encoded by optimized nucleotide sequences. In contrast to plasma derived fibrinogen, the fibrinogen preparation produced by this method will be rather homogeneous because specific fibrinogen chains are produced. The method allows for the production of fibrinogen preparations which consist for more than 10%, 20%, 30%, 40%, 50%, 60%, 70%, 80%, 90%, preferably more than 95%, 98% or 99% of variants, which are present in plasma in only low amounts.

In another aspect, the present invention relates to the use of nucleotide sequences according to the invention in the preparation of fibrinogen for several medical applications. In one application, the nucleotide sequences according to the invention are used to prepare fibrinogen for use in fibrin sealants which are clinically applied during surgical interventions to stop bleeding and to decrease blood and fluid loss. In another application, the nucleotide sequences according to the invention may be used to prepare fibrinogen to facilitate tissue adherence by using the agglutination property of fibrin and to improve wound healing. In yet another application, the nucleotide sequences according to the invention may be used to prepare fibrinogen which is used clinically for the treatment of acute bleeding episodes in patients with congenital or acquired (e.g. through hemorrhage after trauma or during surgery) fibrinogen deficiency by intravenous administration of fibrinogen. Marketed plasma derived fibrinogen preparations are Riastap (CSL Behring LLC; marketed in the US) and Haemocomplettan (CSL Behring AG; marketed in Europe). Recombinant fibrinogen preparations would have several advantages over plasma derived preparations, including a preferred safety profile, unlimited supply and the possibility to manufacture the fibrinogen variant with the preferred activity profile for this specific indication a pure way.

MW: the Molecular Weight Marker (Bench Mark, Invitrogen)

ERL FIB3: plasma derived fibrinogen (ERL), either treated with PNGase F (+) or non-treated (−) with PNGase F. PER.C6 fbg: PER.C6 derived fibrinogen, either treated with PNGase F (+) or non-treated (−) with PNGase F. 2 .mu.g of fibrinogen was loaded per lane; staining was done using Coomassie Blue. Analysis was performed using a reduced 10% BisTris gel (NuPage, Invitrogen).

Figure 7:
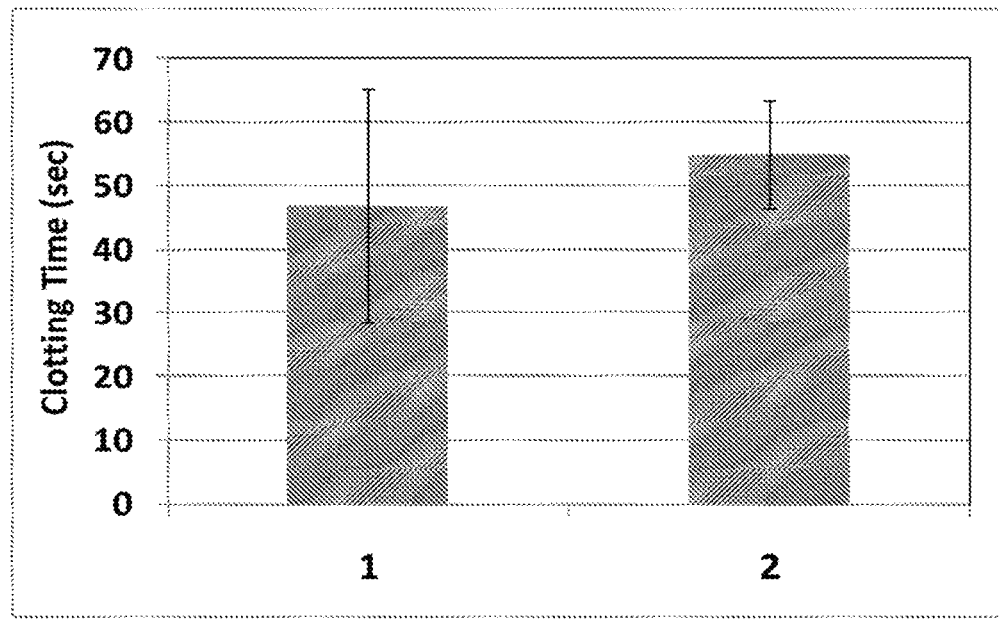

FIG. 7 ROTEM analysis: clotting time. Clotting time was determined by ROTEM analysis. 200 .mu.l of pooled normal (citrate) plasma or 100 .mu.l of pooled normal (citrate) plasma mixed 1:1 with Haemocomplettan (CSL Behring GmbH, Marburg, Germany) or PER.C6 fibrinogen (both 2 mg/ml in TBS). CaCl.sub.2 was added to a final concentration of 17 mM. To start clotting .alpha.-thrombin was added to a final concentration of 1 IU/ml. Total reaction volume was 240 .mu.l. The figure displays the clotting time (seconds) for plasma mixed 1:1 with fibrinogen:
1. Plasma derived fibrinogen (CSL Behring, Marburg, Germany)
2. PER.C6 derived fibrinogen All measurements were done in duplicate.

Figure 8:
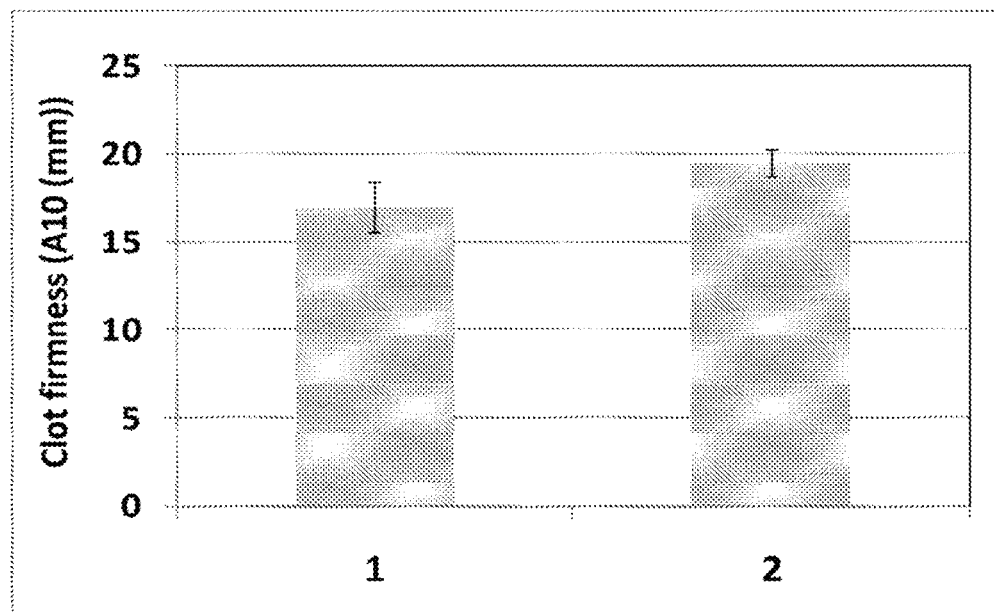

FIG. 8 ROTEM analysis: clot firmness. Clot firmness was determined by ROTEM analysis. The figure expresses the A10 value (mm), which is the firmness of the clot at time 10 minutes, for plasma mixed 1:1 with fibrinogen. Experimental details are the same as described in the legend of FIG. 7.
1. Plasma derived fibrinogen (CSL Behring, Marburg, Germany)
2. PER.C6 derived fibrinogen.

All measurements were done in duplicate.

Figure 9:
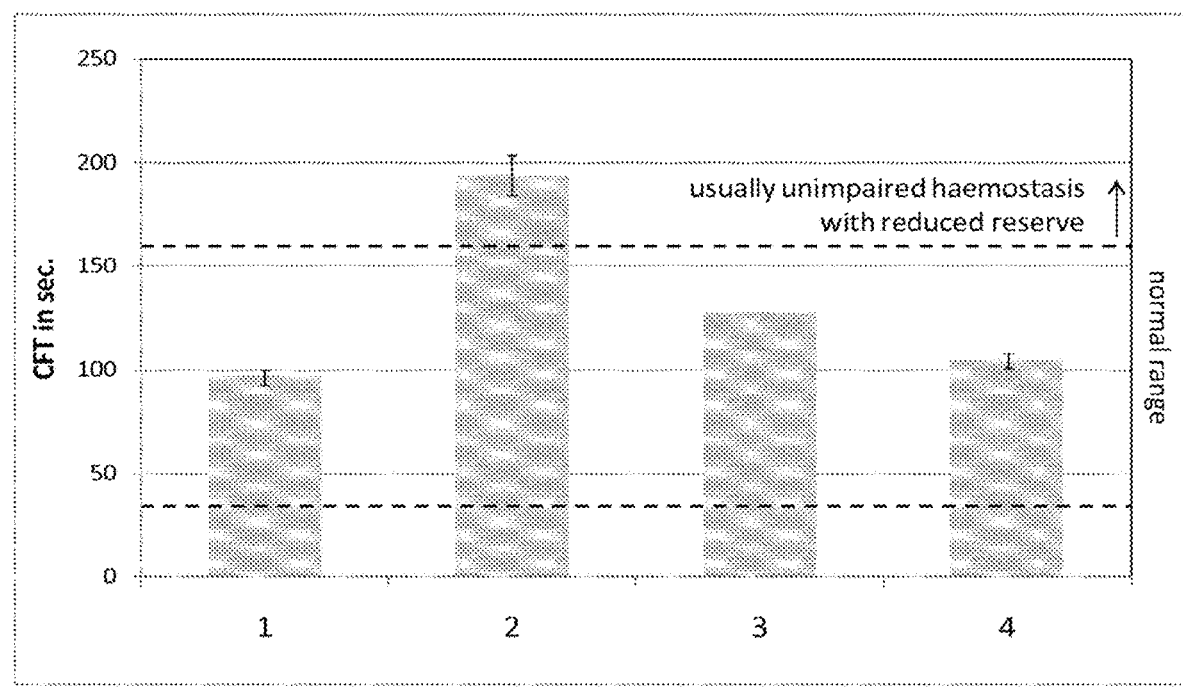

FIG. 9 ROTEM analysis: clot formation time. Citrated blood from a healthy individual was either or not diluted with Ringer's lactate (Baxter, Utrecht, The Netherlands). Subsequently, blood diluted with Ringer's lactate was either or not (control) replenished with plasma derived or recombinant fibrinogen.

The figure display the following:
1. 300 .mu.l blood
2. 150 .mu.l blood, 100 .mu.l Ringer's lactate (RL), 50 .mu.l TBS
3. 150 .mu.l blood, 100 .mu.l RL, 50 .mu.l Haemocomplettan 6.5 mg/ml (1.1 mg/ml final conc.)
4. 150 .mu.l blood, 100 .mu.l RL, 50 .mu.l recombinant hFbg 6.5 mg/ml (1.1 mg/ml final conc.)

In all conditions 20 .mu.l star-TEM and 20 .mu.l ex-TEM reagent (Pentapharm GmbH, Munich, Germany) was used to start coagulation.

Normal range (35-160 sec) are values found for healthy individuals. CFT values of 160-220 sec are found in patients with normally unimpaired haemostasis but with reduced reserve.

Figure 10:
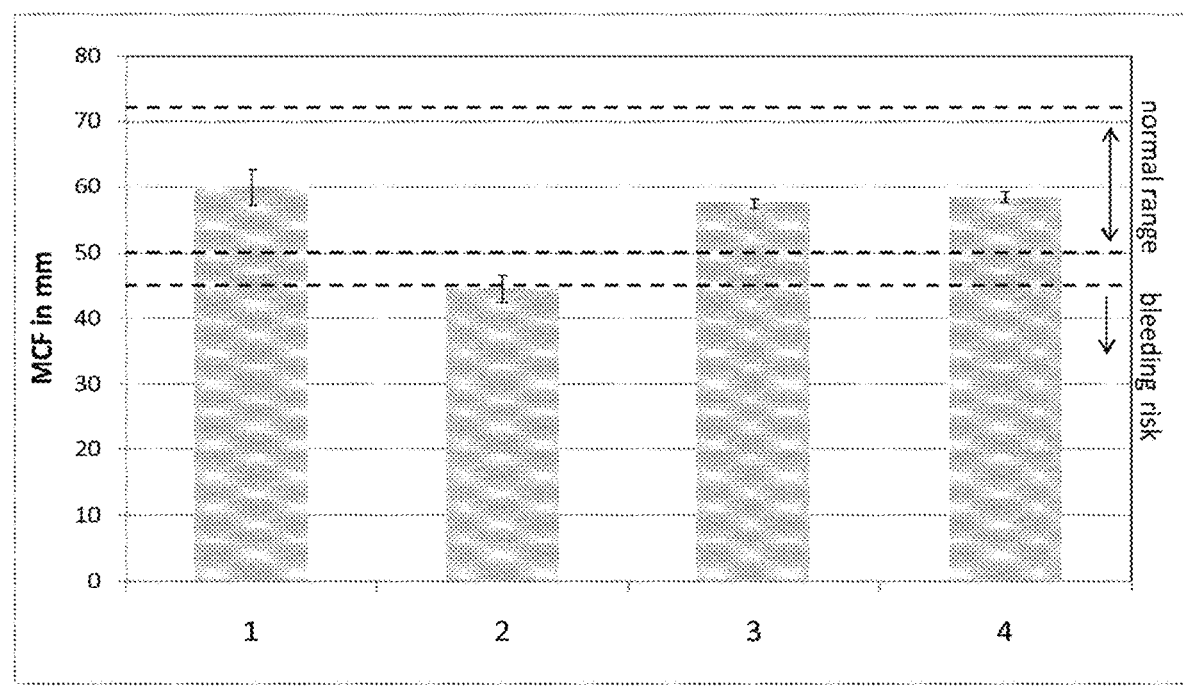

FIG. 10 ROTEM analysis: clot firmness. Citrated blood from a healthy individual was either or not diluted with Ringer's lactate (Baxter, Utrecht, The Netherlands). Subsequently, blood diluted with Ringer's lactate was either or not (control) replenished with plasma derived or recombinant fibrinogen.

Measurement conditions were as follows:
1. 300 .mu.l blood
2. 150 .mu.l blood, 100 .mu.l Ringer's lactate (RL), 50 .mu.l TBS 3. 150 .mu.l blood, 100 .mu.l RL, 50 .mu.l Haemocomplettan 6.5 mg/ml (1.1 mg/ml final conc.)
4. 150 .mu.l blood, 100 .mu.l RL, 50 .mu.l recombinant hFbg 6.5 mg/ml (1.1 mg/ml final conc.)

In all conditions 20 .mu.l star-TEM and 20 .mu.l ex-TEM reagent (Pentapharm GmbH, Munich, Germany) was used to start coagulation.

Normal range (53-72 mm) are values found for healthy patients without coagulation disorders. MCF values of 45-40 mm found in patients indicate a bleeding risk.

EXAMPLES

Example 1: Preparation of Optimized cDNA Constructs cDNAs coding for human fibrinogen polypeptide chains A.alpha., B.beta., .gamma., A.alpha.-extended (Fib420) and .gamma.' were synthesized in both wild type (in this Example referring to the non-optimized format) and codon optimized format by GeneArt (Regensburg, Germany): (i) cis-acting sites (splice sites, poly(A) signals) were removed; (ii) repeat sequence of A.alpha. chain was modified; (iii) GC content was increased for prolonged mRNA half life; (iv) Codon usage was adapted to CHO (codon adaption index-CAI→0.95). Wildtype reference used were NM.sub.-021871 for the alpha chain, NM.sub.-005141 for the beta chain and NM.sub.-000509 for the gamma chain.

The cDNAs coding for A.alpha. (SEQ ID NO. 1), B.beta. (SEQ ID No. 2) and .gamma. (SEQ ID NO. 3) chain in wild type format and for optimized A.alpha. (SEQ ID NO. 4), B.beta. (SEQ ID No. 5) and .gamma. (SEQ ID NO. 6) cDNAs were compared and the results are shown in Table 1. Optimized A.alpha.-extended (Fib420) (SEQ ID NO. 7) and .gamma.' sequences (SEQ ID NO. 12) are also displayed in Table I.

Wild type alpha (SEQ ID no. 1), beta (SEQ ID NO. 2) and gamma (SEQ ID NO. 3) chain cDNA and optimized alpha (SEQ ID no. 4), beta (SEQ ID no. 5), and gamma (SEQ ID no. 6), chain cDNA were subcloned in pcDNA3.1 deriviates. Both − wildtype and optimized-A.alpha.-chains, and A.alpha.-extended (Fib420) in pcDNA3.1(+) neo, both B.beta. chains in pcDNA3.1(+)hygro and both .gamma. chains in pcDNA3.1(−)hygro (Invitrogen, Carlsbad, USA). Optimized .gamma.'-chain was subcloned in pcDNA3.1(+) hygro.

TABLE 1

| Fibrinogen chain | Match (%) Wt/opt | Codon Adaptation Index (CAI) Wild type | optimized | GC content (%) wild-type | optimized |
|---|---|---|---|---|---|
| Aα chain | 72 | 0.71 | 0.97 | 48 | 65 |
| Bβ chain | 77 | 0.69 | 0.96 | 45 | 60 |
| γ chain | 76 | 0.68 | 0.97 | 42 | 60 |
| Fib 420 Aα chain | 72 | 0.71 | 0.98 | 48 | 63 |
| γ' chain | 75 | n.d. | 0.97 | 42 | 60 |

Example 2: Transient Expression of Codon-Optimized and Wild-Type Fibrinogen Sequences in CHO Cells To verify whether the optimized sequences improved protein expression, transient transfections were done in CHO-S cells (Invitrogen, Carlsbad, USA), according to the manufacturer's instructions. Briefly, CHO-S cells were seeded on the day prior to transfection at 0.6.times.10.sup.6 cells/ml in FreeStyle culture medium supplemented with 8 mM L-glutamine. On the day of transfection, cells were diluted to a concentration of 1.times.10.sup.6 cells/ml in 15 ml medium in a 125 ml shake flask (Corning Life Sciences, Corning, USA). A total of 18.75 pg expression plasmid (6.25 pg for each individual chain) was mixed with 0.3 ml Opti Pro SFM. Subsequently 0.3 ml FreeStyle MAX Transfection Reagent (16.times. diluted in Opti Pro SFM) was added and mixed gently. After a 10 minute incubation at room temperature the DNA-FreeStyle MAX mix was gently added to the CHO-S cells, slowly swirling the shake flask. The experiment was performed in duplicate.

Transfected cells were incubated at 37.degree. C., 5% CO.sub.2 on an orbital shaker platform rotating at 125 rpm. On day 1, 2, 3, and 6 post transfection samples were collected to measure recombinant fibrinogen expression.

Protein expression was measured with an ELISA specific for human fibrinogen. Certified Maxisorb Elisa plates (Nunc, Thermofisher Scientific, Roskilde, Denmark) were coated overnight with 100 .mu.l 10 .mu.g/ml G8 monoclonal antibody (TNO KvL, Leiden, The Netherlands) raised against human fibrinogen (Hoegee-de Nobel et al. (1988) Thromb. Haemost. 60(3) 415) in PBS (Invitrogen) at 4.degree. C. Then the plates were washed with PBST (PBS/0.05% Tween20 tablets, Calbiochem, EMD, San Diego, USA) and 100 .mu.l of either culture supernatant sample or fibrinogen standard were added. The fibrinogen standard contained fibrinogen (FIB3 Human Fibrinogen, Enzyme Research Laboratories (ERL), Swansea, UK) dissolved and diluted in PBST at the following concentrations: 100-75-50-25-12.5-6.25-3.125-0 ng/ml. Tissue culture supernatant samples were diluted 1:10-1:500 in PBST. After 1 hour incubation at room temperature the plates were washed 3 times with 200 .mu.l PBST per well and tapped dry on a paper towel. Then 100 .mu.l of HRP conjugated Y18 monoclonal antibody (TNO KvL, Leiden, The Netherlands), diluted 1:10.000 in PBST, was added. This was incubated for 1 hour at room temperature, followed by washing the plates 4 times with 200 .mu.l PBST per well; to after each wash step the plates were tapped dry on a paper towel. Then, 100 .mu.l TMB Ultra (Pierce, Thermofisher Scientific, Rockford, USA) was added to each well, followed by an incubation of 4-30 minutes at room temperature. The reaction was stopped by addition of 100 .mu.l 2M H.sub.2SO.sub.4 (Merck KgaA, Darmstadt, Germany) to each well and the OD450 was determined using an ELISA plate reader.

Figure 1:
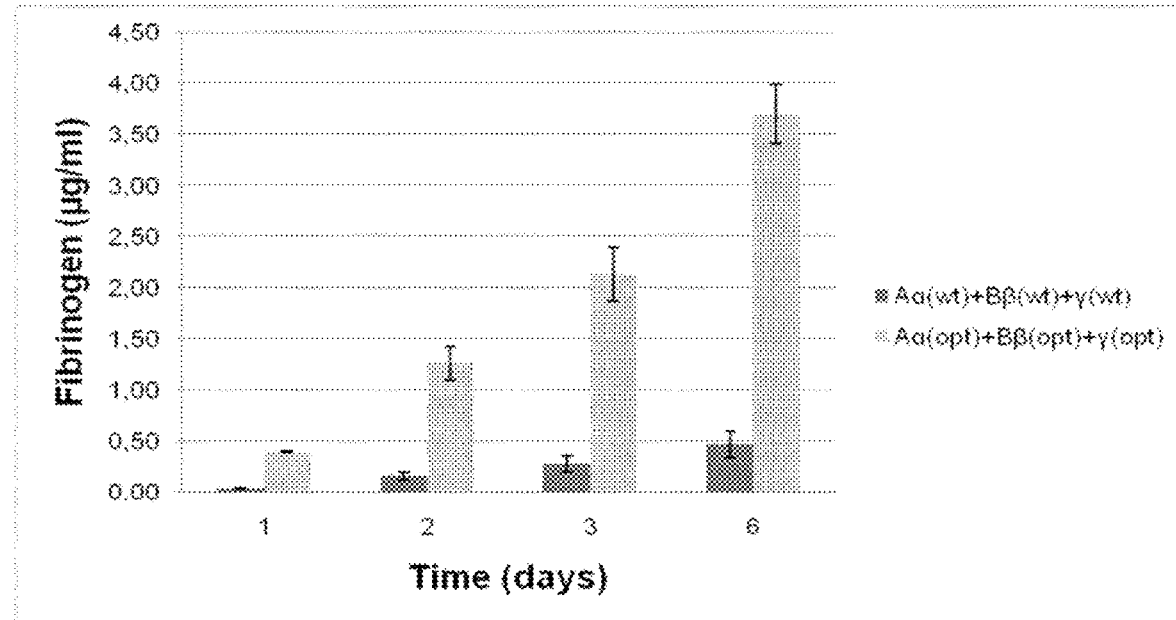
FIG. 1 Levels of expression of recombinant human fibrinogen 1, 2, 3 and 6 days after transfection of CHO cells with wild-type and codon optimized constructs encoding the A.alpha., B.beta. and .gamma. chain. The experiment was done in duplicate. (opt) optimized sequences; (wt) wild-type sequences.

The results are shown in FIG. 1. The data clearly show that the optimized sequences improve the expression of fibrinogen dramatically at all time points where samples were analysed. The increase in expression level for optimized constructs ranges from 7.9-10.5 times.

Example 3: Transient Expression of Codon-Optimized Fibrinogen 420 in Serum-Free Cultured CHO Cells Transfection and analysis were performed as described in Example 2. The extended A.alpha.-chain cDNA sequence used in this experiment is an optimized extended A.alpha. sequence (SEQ ID No. 7) and codes for a secreted polypeptide of 847 amino acids (SEQ ID No. 11).

Figure 2:
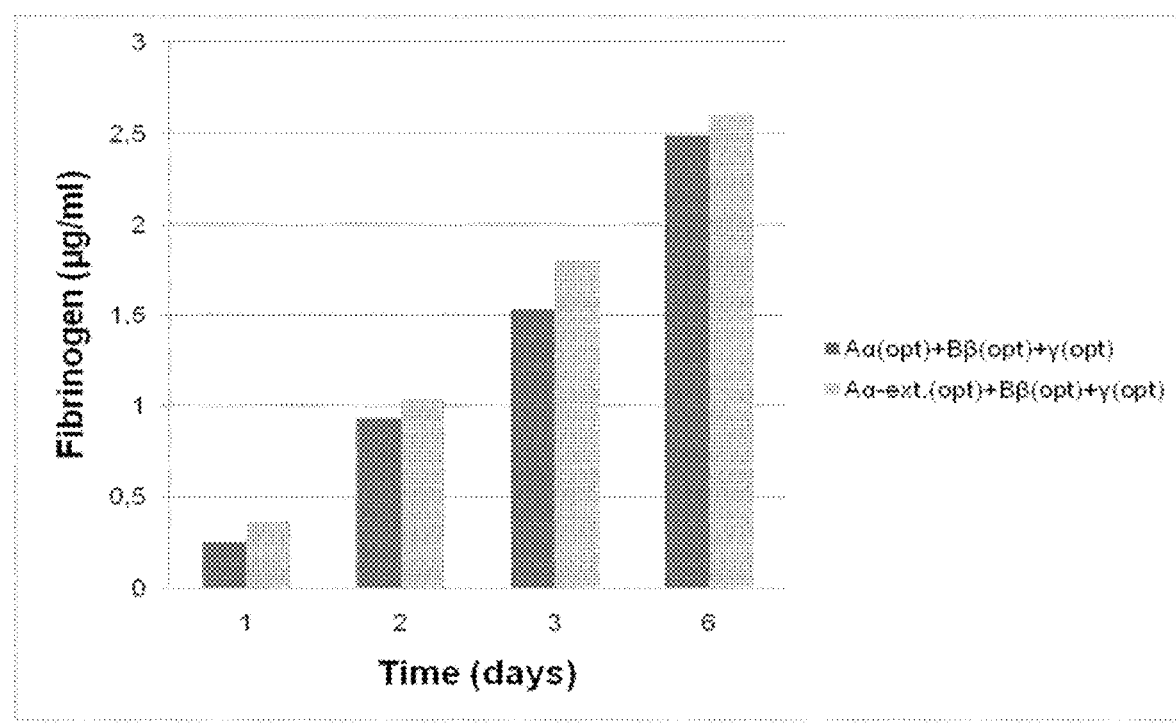
FIG. 2 Levels of expression of recombinant human fibrinogen at 1, 2, 3 and 6 days after transfection of CHO cells with codon optimized constructs encoding the A.alpha., B.beta. and .gamma. chain and codon optimized constructs (marked as A.alpha.(opt)+B.beta.(opt)+.gamma.(opt)) with A.alpha.-extended, B.beta. and .gamma. chain (marked as A.alpha.-ext.(opt)+B.beta.(opt)+.gamma.(opt)). The experiment was done in duplicate.

The results are shown in FIG. 2 and clearly show that the expression levels of a fibrinogen variant, in this case the Fib420 variant with extended A.alpha. chains, are in the same range as the enhanced levels for the optimized 'wild-type' A.alpha.-chain variant.

Example 4: Generation of Cho Cells Stably Expressing Human Fibrinogen from Codon-Optimized Fibrinogen cDNAs Under Serum-Free Conditions For the cell-line generation described in this report the sequence-optimized pcDNA3.1 derived plasmids were used, as described in Example 1. Briefly, CHO-S cells (Invitrogen) were subcultured in FreeStyle medium (Invitrogen) supplemented with 8 mM L-glutamine (Invitrogen) according to the manufacturer's instruction. Routinely cells were cultured in a 125 ml shake flask format containing 10% (v/v) culture medium (=12.5 ml). The cultures were placed in a humidified incubator at 37.degree. C. and 5% $CO_2$ on a horizontally shaking platform at 125 rpm. Transfections of CHO-S cells (invitrogen) were performed according to the manufacturer's instructions. After transfection the cultures were incubated overnight in a humidified incubator at 37.degree. C. and 5% $CO_2$ on a horizontally shaking platform at 125 rpm.

The day following the transfection, the cells were counted, and seeded into 96-well plates (seeding density 200 cells/well) in FreeStyle medium supplemented with 8 to mM L glutamine and the selection agents Geneticin (Invitrogen) and Hygromycin B (Invitrogen) (both at a final concentration of 500 .mu.g/ml: from here on "selection medium"). Culture volume in each well was 100-200 .mu.l. Plates were placed in a humidified incubator at 37.degree. C. and 5% $CO_2$ under stationary conditions. The medium was changed twice a week with 100 .mu.l selection medium. The plates were screened for cell growth microscopically. After 10 days resistant clones became apparent. These clones were transferred into 48 well plates containing 500 .mu.l selection medium.

When clones reached approximately 50% confluence the medium was sampled and stored at −20.degree. C. until ELISA analysis for fibrinogen expression levels was performed (see example 2). Based on ELISA results clones positive for fibrinogen were sub-cultured to 6-well plates. Again at approximately 50% confluence medium of each clone was sampled and analysed for expression by ELISA. Based on the ELISA data, selected high expressing clones were transferred to T25 flasks and 3-5 days later to T75 $cm^2$ flasks. Then, cells were transferred to shaker cultures, where they were inoculated at a concentration of $0.2 \times 10^6$ viable cells/ml in 125 ml shake flasks containing 12.5 ml selection medium. Flasks were placed on an ELMI horizontal shaker at 125 rpm in a humidified incubator at 37.degree. C. and 5% $CO_2$. After reaching cell densities of more than $0.5 \times 10^6$ viable cells/ml, the cells were sub-cultured into a new 125 ml shake flask with fresh medium three times a week at an inoculation concentration of $0.2 \times 10^6$ viable cells/ml until reproducible growth characteristics were established (usually within 2 weeks). Cultures of selected clones were maintained in selection medium.

For batch testing, shaker cultures were started of the selected clones in 12.5 ml FreeStyle medium supplemented with 8 mM L-glutamine in 125 ml shake flasks. The cultures were inoculated at $0.2 \times 10^6$ viable cells/ml. Flasks were placed on the DOS-10-ELMI horizontal shaker at 125 rpm at 37.degree. C. and 5% $CO_2$ in a humidified incubator. Samples were collected on day 1, 2, 3, 4, and 7 post seeding, and total cell count and viability (by Trypan Blue staining) were determined. The samples were cleared from cells by 300.times.g centrifugation and supernatants were stored at −20.degree. C. until fibrinogen concentrations could be determined.

For Western blotting, samples containing fibrinogen were mixed with 5 .mu.l 4.times. concentrated NuPAGE LDS sample buffer (Invitrogen, Paisley, UK) and 2 .mu.l 10.times. concentrated NuPAGE sample reducing agent (Invitrogen). The final volume was adjusted to 20 .mu.l with deionized water (Invitrogen/Gibco). Samples were heated for 10 minutes at 70.degree. C. and loaded on a NuPAGE Novex gel (10%; BisTris Mini gel, Invitrogen), according to the instructions of the manufacturer. The gel was run for 1 hour at 200 Volt. Blotting buffer was prepared by mixing 44 ml 25.times. Novex Tris-Glycine Transfer Buffer (Invitrogen), 836 ml of demiwater and 220 ml of methanol (Merck). The solution was precooled for a minimum of 30 minutes at −20.degree. C. A piece of PVDF membrane (Pierce) is activated for about 15 seconds in methanol. The membrane, 6 pieces of Gel Blotting Paper and 2 blotting pads were then incubated in blot buffer for a few minutes. The membrane was placed on the gel in a blotcassette which was put in a blotting chamber (Bio-Rad Laboratories, Hercules, USA) holding a cold pack frozen at −20.degree. C. Protein transfer was performed at 100 Volts across the gel/membrane assembly for 1 hour, To visualize the fibrinogen bands on the membrane, the blot was incubated in 50 ml blocking buffer (3% Low fat milk powder (Elk, Campina, Meppel, The Netherlands) in PBS) on a platform shaker. Then, the blot was washed for 10 minutes in 50 ml washing buffer (0.05% Tween20 in PBS) and incubated for 1 hour with 10 ml of blocking buffer containing 1/2000 dilution of the HRP conjugated monoclonal antibody Y18/PO (Koppert et al. (1985) 66, 503). Then the blot was washed 2.times. short (less than 1 minute), 1.times.15 min, and 3.times.5 min. in 50 ml washbuffer, followed by a 10 min incubation in 50 ml PBS.

The bands were visualized with ECL (cat#32209, Pierce). The image was captured using a ChemiDoc-It Imaging System (UVP, California, US).

Multiple rounds of generation of stable clones were performed. Only clones which produced more than 3 picogram per cell per day (pcd) in 7 days batch cultures were collected. Some clones produced more than 5 pcd in 7 days batch cultures.

Figure 3:
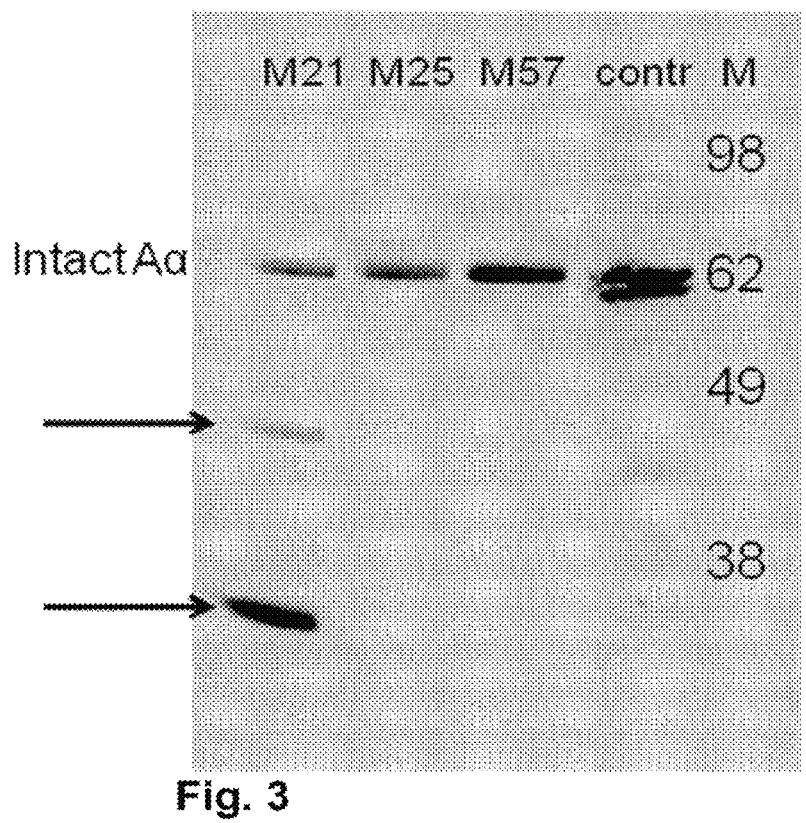
FIG. 3 Western blot analysis of culture supernatant from batch runs of clones M21, M25 and M57, which express recombinant human fibrinogen. The control lane (contr) contains plasma derived wild-type fibrinogen (FIB3, Enzyme Research Laboratories). The arrows indicate the breakdown products of the A.alpha. chain.

As indicated before, clones were tested both for fibrinogen production as well as for quality of the produced fibrinogen. Some clones produced high levels of intact fibrinogen, other generated intact product but also showed degradation products. The A.alpha.-chain is most sensitive to proteolysis as compared to the B.beta. and .gamma., so the primary screening tool screening was in first instance focused on testing the A.alpha. chain for integrity. A typical example is shown in FIG. 3, where clone M21 clearly shows degradation of the A.alpha. chain, whereas M25 and M57 do not. Western blot analysis of these samples for integrity of the B.beta. and .gamma. proved that these chains were still intact, even if the A.alpha. chain showed proteolytic breakdown.

Example 5: Generation of Stable Cell Lines Expressing Human Variant Fib 420

Stable cell lines expressing a variant of human fibrinogen, viz. the Fib 420 variant which has an extended A.alpha. chain (847 amino acids rather than 625) were generated. A codon optimized construct (SEQ ID No. 7) was used and clones were generated under serum-free conditions, as described in Example 5.

The supernatant of two positive clones which produced more than 3 pcd in a 7 days batch culture were checked for intact extended A.alpha. chain (Fib420) using Western blot analysis. It was clear (FIG. 4) that even in the high producing clones the A.alpha. chain of Fib420 was extended and intact.

Example 6: Generation of PER.C6 Cells Stably Expressing Human Fibrinogen from Codon-Optimized Fibrinogen cDNAs Under Serum-Free Conditions PER.C6 cells (Fallaux et al. (1998) Hum. Gene Ther. 9(13) 1909) were used as a host for the expression of recombinant human fibrinogen. Briefly, PER.C6 cells were cultured in suspension in mAb medium (SAFC, Hampshire, UK) and transfected using the AMAXA (Lonza, Cologne, Germany) nucleofection device (program A-27, using Nucleofector kit T with three vectors encoding the three different chains of the human fibrinogen protein (A.alpha.-, B.beta.-, and .gamma. chain) and containing the optimized cDNA chains (SEQ ID no. 4, SEQ ID no. 5, and SEQ ID no. 6, resp).

After nucleofection, the cells were cultured for 1 day in T-flasks and subsequently seeded in 96 well plates (Greiner, Alphen a/d Rijn, The Netherlands) at a density of 1000-3000 cells/well. Then mAb medium containing 125 .mu.g/ml Geneticin (Invitrogen) was added. After approximately three weeks, clones in about 10-30% of individual wells of the 96-well plate appeared, which were subsequently expanded to 48-, 24- and 6 wells plates and then subcultured into T25 and T80 culture flasks. Throughout the expansion the cultures were screened for expression levels of human fibrinogen. Low and non-expressing cells were discarded. Subsequently cells were cultured in shake flasks (125 ml, Corning).

In total, 579 clones were identified in 96-wells plates. Based on fibrinogen expression levels throughout expansion, 43 clones were selected and subcultured to shake flasks. 10 out of these 43 recombinant human fibrinogen producing PER.C6 cell lines were selected for initial batch testing, based on growth- and production characteristics. Batch testing of the 6 selected PER.C6® cell lines in VPRO medium (SAFC) showed volumetric production levels up to 279 mg/L recombinant human fibrinogen, and a specific productivity of 19.8 pcd. Finally a batch culture in VPRO medium was performed with a medium change at time of sampling, which resulted in cumulative volumetric production levels of up to 515 mg/L recombinant human fibrinogen.

Example 7: Generation of Stable PER.C6 Cell Lines Expressing Human Fibrinogen with an A.Alpha.-Chain of 610 Amino Acids In order to generate an expression plasmid encoding the A.alpha.610 of the predominant form of plasma fibrinogen in the blood circulation, a cDNA fragment (SEQUENCE ID 8), optimized as described before, encoding amino acids 1-610 of the A.alpha. chain was cloned into expression plasmid pcDNA3.1(+) neo, according to standard procedures. The generation of PER.C6 cell lines producing recombinant human fibrinogen is similar as described before (see example 6). Sequences used for A.alpha.-, B.beta.-, and .gamma. chain are SEQ ID no. 8, SEQ ID no. 5, and SEQ ID no. 6, resp.

After transfection of PER.C6 cells and plating in 96-well plates, 310 clones were transferred and screened in 48-well plates. At the end of the expansion path, 24 out of these 310 were transferred to shaker flasks, of which after an initial batch test, 8 were selected for stability and productivity testing in batch culture.

Yields in batch culture were similar to yields obtained with cell lines that express the A.alpha.-chain in 625 amino acid format, clearly demonstrating that expression of A.alpha. chains from a cDNA coding for a 610 amino form does not impair expressions levels.

Protein analysis using SDS-PAGE and Western blotting analysis indicated that the recombinant fibrinogen was produced in intact format.

Example 8: PER.C6 Cell Lines Expressing Recombinant Human Fibrinogen Based on Extended A.Alpha.-Chain (Fib420 Variant)

The generation of PER.C6 cell lines producing recombinant human fibrinogen is similar as described before (see examples 6 and 7). In summary, sequences used for A.alpha.-, B.beta.-, and .gamma. chain are SEQ ID no. 7, SEQ ID no. 5, and SEQ ID no. 6, resp.

After transfection and plating in 96-well plates, 325 clones were transferred and screened in 48-well plates. At the end of the expansion path, 24 clones were transferred to shaker flasks, of which 8 were selected for stability and expression analysis in continued batch culture testing.

Figure 4:
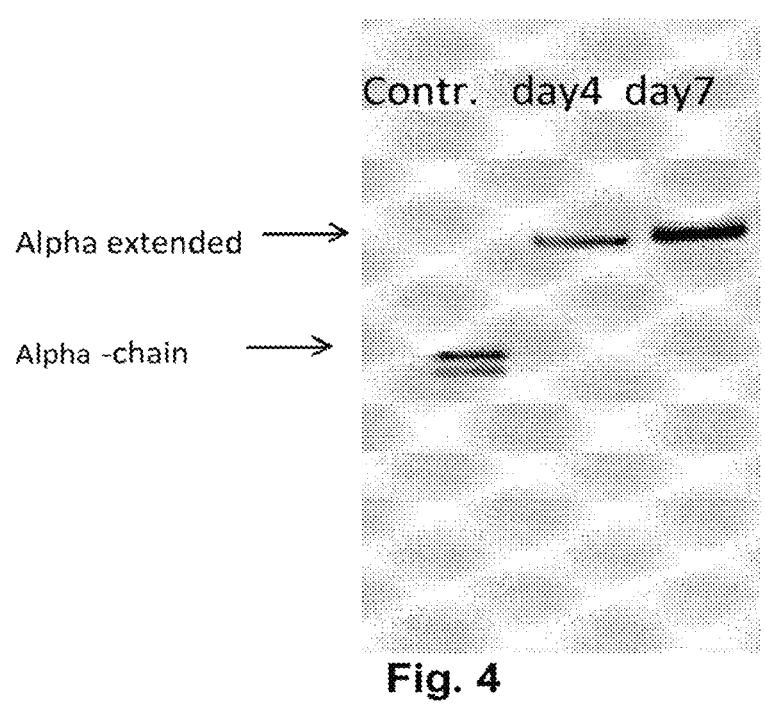
FIG. 4 Western blot analysis of culture supernatant from a batch run of clone P40 expressing variant human fibrinogen (Fib420), which has an extended A.alpha. chain. Lane 1 is a control containing plasma derived wild-type fibrinogen (FIB3, Enzyme Research Laboratories). Lanes 2 and 3 contain culture supernatant of clone P40 A.alpha.-extended, taken at day 4 and at day 7 of a batch run, respectively.

Yields in batch culture were similar to yields obtained with cell lines that express the A.alpha.-chain in 610 or 625 amino acid format, indicating that the extension of the A.alpha.-chain does not impair expression levels. This was not expected on forehand, as plasma derived fibrinogen only contains 1-3% of extended A.alpha.-chain as compared to 610/625 A.alpha.-chain containing fibrinogen. Protein analysis using SDS-PAGE and Western blotting analysis indicate that the recombinant fibrinogen is produced in intact format, with the .alpha.-chain having the expected size (similar to CHO produced A.alpha.-chain from Fib420 as shown in FIG. 4).

Example 9: Transient Expression of .Gamma.' Codon-Optimized Fibrinogen in Serum-Free Cultured CHO Cells Transient transfection and analysis were performed as described in Example 2. The extended .gamma.'-chain cDNA sequence used in this experiment is an optimized extended .gamma.' sequence (SEQ ID No. 12) and codes for a polypeptide of 453 amino acids. After removal of the signal peptide, a secreted polypeptide of 427 amino acids (amino acids 27 to 453 of SEQ ID NO. 13).

Figure 5:
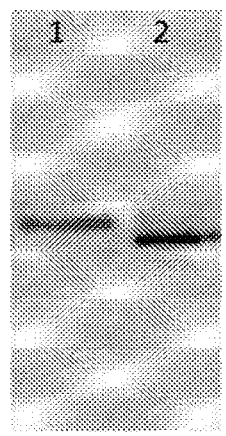
FIG. 5 Western blot analysis of culture supernatant of PER.C6 cells that were transiently transfected with .gamma.' containing human fibrinogen (details are described in example 9). Lane 1 contains culture supernatant of PER.C6 cells expressing recombinant .gamma.' fibrinogen. Lane 2 is a control, containing plasma derived wild-type fibrinogen (FIB3, Enzyme Research Laboratories).

The results showed that the expression levels of the fibrinogen variant with the .gamma.' chains are in the same range as the enhanced levels for the optimized 'wild-type' variant. Culture supernatant was analyzed by Western blotting analysis. The results (FIG. 5) show that .gamma.'-chain recombinant fibrinogen, in lane 1, runs slower than 'wild-type' fibrinogen, in lane 2. This indicates that the .gamma.'-chain in recombinant fibrinogen is extended as compared to .gamma.-chain in plasma derived fibrinogen and that the .gamma.'-chain is intact and not degraded.

Example 10: Purification of Recombinant Human Fibrinogen

Recombinant human fibrinogen from Example 6 was purified from cell culture supernatant according to standard methods. Briefly, (NH.sub.4)2SO.sub.4 was added to the culture supernatant to 40% saturation and the precipitate is collected by centrifugation. Subsequently, the precipitate was dissolved in TBS (50 mM Tris-HCl, pH7.4, 100 mM NaCl), diluted (10-fold) in loading buffer (5 mM Tris-HCl pH 7.4, 0.01% Tween-20, 0.5M (NH.sub.4)2SO.sub.4) and loaded on a HiTrap Butyl FF (20 ml) (GE Healthcare, Uppsala, Sweden) Hydrophobic Interaction Column (HIC). Bound protein was eluted by loading buffer containing a gradient of (NH.sub.4)2SO.sub.4 of 0.5-0 M (NH.sub.4)2SO.sub.4 in 20 column volumes. The peak fractions of the HIC purification were subjected to a buffer change by dialysis versus TMAE loading buffer (5 mM Tris-HCl pH 8.5, 0.01% Tween-20) and subsequently loaded on a Fractogel EMD TMAE (m) 40-90 .mu.m (20 ml) (Merck KGaA, Darmstadt, Germany) Ion Exchange Column. Recombinant human fibrinogen was subsequently eluted using a continuous salt gradient of 0-1 M NaCl in 20 column volumes.

Recombinant human fibrinogen in the peak fractions was precipitated again by adding (NH.sub.4).sub.2SO.sub.4 to 40% saturation and collected by centrifugation. Finally the material was dissolved in TBS (50 mM Tris-HCl, pH7.4, 100 mM NaCl) and dialysed against TBS to remove any remaining (NH.sub.4).sub.2SO.sub.4.

Example 11: Functionality of Recombinant Fibrinogen

Purified recombinant PER.C6 fibrinogen, as produced by cell lines generated in Example 6, was subjected to a number of tests to evaluate it's quality and functionality and to compare it with plasma derived fibrinogen. N-glycosylation of fibrinogen was tested by treatment of fibrinogen with PNGase F, which is an amidase that removes N-linked carbohydrate structures from proteins (Maley, F. et al. (1989) Anal. Biochem. 180, 195). Samples of purified fibrinogen, derived from PER.C6 cultures, as well as plasma derived fibrinogen (FIB3 Human Fibrinogen, ERL) were treated with PNGase F (New England Biolabs, Ipswich, Mass., US), according to the manufacturer's instructions.

Figure 6:
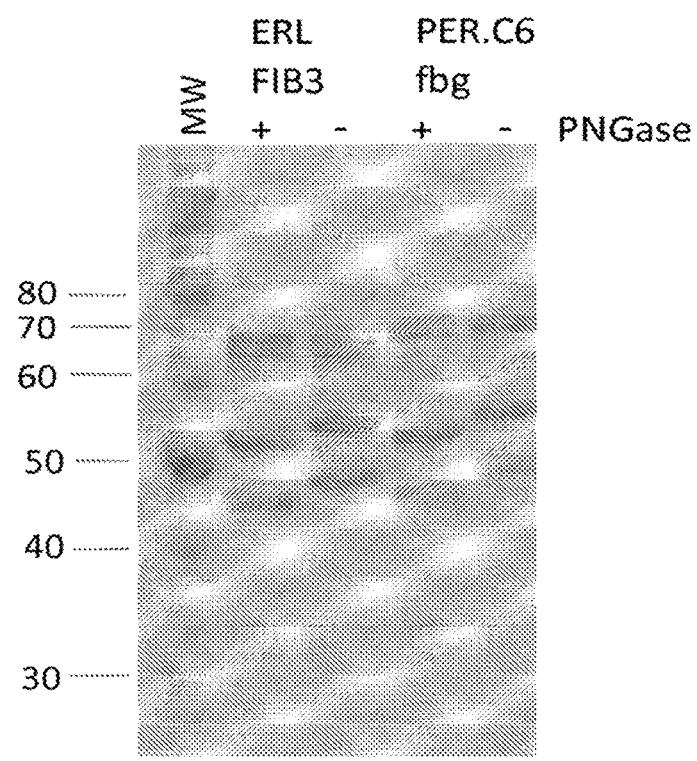
FIG. 6 Analysis of fibrinogen for N-glycosylation by PNGase F treatment followed by SDS-PAGE analysis. The lanes are loaded as follows.

The results (FIG. 6) indicate that PNGase F treatment results in a decreased molecular mass for the B.beta.- and .gamma.-chains, as determined by SDS-PAGE, for both plasma derived FIB3 (ERL) and PER.C6 based fibrinogen. This is consistent with the fact that both chains contain one N-glycosylation site (Henschen-Edman (2001) Ann. N.Y. Acad. Sci. USA 936, 580). The data show that both pre- and post PNGase F treatment, distinct single bands are visible for both the B.beta.- and .gamma.-chain. This indicates that, as for plasma derived fibrinogen, all of these chains in recombinant fibrinogen are glycosylated. The A.alpha.-chain of human fibrinogen contains no N-glycans, hence the molecular weight is not changed upon PNGase F treatment. In conclusion, these data indicate that the N-glycosylation pattern of PER.C6 based fibrinogen is similar to the plasma derived counterpart.

Biological activity of PER.C6 derived fibrinogen was further tested in a polymerization assay, carried out as described by Koopman et al. (1992) Blood 80(8):1972. The results obtained were similar to those obtained with CHO-derived human fibrinogen. The assay measures the polymerization of fibrinogen under the action of thrombin to form fibrin. Polymerization is measured by recording OD350 nm in time. Polymerisation of recombinant PER.C6 fibrinogen in plasma was equal to plasma and CHO-derived fibrinogen.

Clottability of PER.C6 derived fibrinogen, purified as described, was tested by addition of .alpha.-thrombin (7.5 IU/ml) (ERL, Swansea, UK) and CaCl2 (2 mM final concentration), followed by an incubation at 37.degree. C. for 1 hour. The resulting clot was then collected by centrifugation in an Eppendorf vial (15 min, 5000 rpm, eppendorf centrifuge). The supernatant was transferred to a new tube and the clot was dissolved in alkalic urea. Protein was measured in the supernatant and the clot by A280 measurement. Fibrinogen content of the supernatant was measured by ELISA (G8-Y18 antibodies). Results were similar for plasma derived fibrinogen and PER.C6 derived fibrinogen: 97% and 94% of the protein was measured in the dissolved clot (5% and 8% in the supernatant), respectively. No fibrinogen could be detected in the supernatant by ELISA. These results further support biological similarity between plasma derived and recombinant human fibrinogen.

Clotting time and clot firmness of recombinant and plasma derived fibrinogen were measured using ROTEM analysis. ROTEM® (Pentapharm GmbH, Munich, Germany) stands for ROtation ThromboElastoMetry. The technique utilizes a rotating axis submerged in a (blood) sample in a disposable cuvette. Changes in elasticity under different clotting conditions result in a change in the rotation of the axis, which is visualized in a thromboelastogram, reflecting mechanical clot parameters (see e.g. Luddington R. J. (2005) Clin Lab Haematol. 2005 27(2):81). Pooled normal (citrate) plasma was mixed 1:1 with Haemocomplettan (CSL Behring GmbH, Marburg, Germany) or PER.C6 fibrinogen (both 2 mg/ml in TBS). CaCl.sub.2 was added to a final concentration of 17 mM. To start clotting, .alpha.-thrombin was added to a final concentration of 1 IU/ml. Clotting time and clot-firmness were analysed by ROTEM.

Diluting citrated plasma compromises both clotting time and clot firmness. The results indicate that restoring fibrinogen levels in diluted plasma by adding purified fibrinogen restores both clotting time (FIG. 7) and clot firmness (FIG. 8) to the same extent for plasma derived fibrinogen and recombinant fibrinogen. Similar data were obtained with CHO based recombinant fibrinogen.

These results indicate that recombinant human fibrinogen would be a good alternative to supplement fibrinogen deficiency in hereditary fibrinogenemia patients and in patients with an acquired fibrinogen deficiency.

Example 12: ROTEM Analysis in Human Blood

In order to further prove that recombinant human fibrinogen can be used for treatment of patients with fibrinogen deficiency, experiments were carried out in blood from a healthy human individual. Fibrinogen deficiency was mimicked by diluting the blood 1:1 with Ringer's lactate (Baxter, Utrecht, The Netherlands). Then, using ROTEM analysis as described in example 11, clot formation time and clot firmness were determined. To restore the fibrinogen levels in blood that was diluted 1:1 with Ringer's lactate, either plasma derived or recombinant fibrinogen was added.

The data (FIG. 9) indicate that clot formation time of blood diluted with Ringer's lactate was outside the normal range, as in a clinical situation for a patient that has low fibrinogen levels. Addition of either recombinant or plasma derived fibrinogen resulted in restoration of the clot formation time to a level within the normal range. This indicates the potential of recombinant fibrinogen for intra-venous treatment of patients with low to fibrinogen levels.

When blood was diluted with Ringer's lactate maximum clot firmness (MCF) was reduced to a level associated with bleeding risk in patients (FIG. 10). When fibrinogen levels were replenished with plasma derived or recombinant fibrinogen MCF was restored to normal levels, thereby underscoring the potential for use of recombinant fibrinogen for intra-venous treatment of patients with low fibrinogen levels. It is of note, that for approval of Riastap in the US, clinical efficacy was based on a surrogate endpoint, which was Maximum Clot Firmness measured by Thromboelastography.

What is claimed is:

1. A nucleotide sequence which is optimized for expression in a mammalian cell culture system, comprising:
   (i) a nucleotide sequence according to SEQ ID NO. 4 or 7, or a part thereof which comprises nucleotides 60 to 1932 of SEQ ID NO. 4, nucleotides 60 to 1887 of SEQ ID NO. 4 or nucleotides 60-2598 of SEQ ID NO. 7, or a nucleotide sequence which has a sequence which is at least 90% identical to SEQ ID NO. 4 or 7 and which encodes a fibrinogen alpha chain, or
   (ii) a nucleotide sequence according to SEQ ID NO. 5, or the part thereof which comprises nucleotides 93 to 1473 of SEQ ID NO. 5, or a nucleotide sequence which has a sequence which is at least 90% identical to SEQ ID NO. 5 and which encodes a fibrinogen beta chain or
   (iii) a nucleotide sequence according to SEQ ID NO. 6 or 12, or a part thereof which comprises nucleotides 81 to 1311 of SEQ ID NO. 6 or nucleotides 81 to 1359 of SEQ ID NO. 12, or a nucleotide sequence which has a sequence which is at least 90% identical to SEQ ID NO. 6 or 12 and which encodes a fibrinogen gamma chain.

2. The nucleotide sequence of claim 1, wherein the nucleotide sequence is optimized for expression in a COS cell, a BHK cell, a NSO cell, a CHO cell, a SP2/0 or a human cell culture system.

3. A nucleotide sequence according to claim 1 which is optimized for expression in a PER.C6 cell or a HEK293 cell culture system.

4. The nucleotide sequence of claim 1, wherein the nucleotide sequence has a codon adaption index of at least 0.95.

5. The nucleotide sequence of claim 1, wherein the nucleotide sequence has a GC content of at least 55%.

6. The nucleotide sequence of claim 1, wherein the nucleotide sequence contains no cis-acting sites.

7. A nucleotide construct comprising the nucleotide sequence of claim 1.

8. A mammalian cell comprising the nucleotide sequence of claim 1.

* * * * *

SEQUENCE LISTING

<160> NUMBER OF SEQ ID NOS: 13

<210> SEQ ID NO 1
<211> LENGTH: 1932
<212> TYPE: DNA
<213> ORGANISM: Homo sapiens

<400> SEQUENCE: 1

```
atgttttcca tgaggatcgt ctgcctggtc ctaagtgtgg tgggcacagc atggactgca      60
gatagtggtg aaggtgactt tctagctgaa ggaggaggcg tgcgtggccc aagggttgtg     120
gaaagacatc aatctgcctg caaagattca gactggccct tctgctctga tgaagactgg     180
aactacaaat gcccttctgg ctgcaggatg aaagggttga ttgatgaagt caatcaagat     240
tttacaaaca gaataaataa gctcaaaaat tcactatttg aatatcagaa gaacaataag     300
gattctcatt cgttgaccac taatataatg gaaattttga gaggcgattt ttcctcagcc     360
aataaccgtg ataataccta caaccgagtg tcagaggatc tgagaagcag aattgaagtc     420
ctgaagcgca aagtcataga aaaagtacag catatccagc ttctgcaaaa aaatgttagg     480
gcccagttgg ttgatatgaa acgactggag gtggacattg atattaagat ccgatcttgt     540
cgagggtcat gcagtagggc tttagctcgt gaagtagatc tgaaggacta tgaagatcag     600
cagaagcaac ttgaacaggt cattgccaaa gacttacttc cctctagaga taggcaacac     660
ttaccactga taaaaatgaa accagttcca gacttggttc ccggaaattt taagagccag     720
cttcagaagg tacccccaga gtggaaggca ttaacagaca tgccgcagat gagaatggag     780
ttagagagac ctggtggaaa tgagattact cgaggaggct ccacctctta tggaaccgga     840
tcagagacgg aaagccccag gaaccctagc agtgctggaa gctggaactc tgggagctct     900
ggacctggaa gtactggaaa ccgaaaccct gggagctctg gactggagg gactgcaacc     960
tggaaacctg ggagctctgg acctggaagt actggaagct ggaactctgg gagctctgga    1020
actggaagta ctggaaacca aaaccctggg agccctagac ctggtagtac cggaacctgg    1080
aatcctggca gctctgaacg cggaagtgct gggcactgga cctctgagag ctctgtatct    1140
ggtagtactg gacaatggca ctctgaatct ggaagtttta ggccagatag cccaggctct    1200
gggaacgcga ggcctaacaa cccagactgg ggcacatttg aagaggtgtc aggaaatgta    1260
agtccaggga caaggagaga gtaccacaca gaaaaactgg tcacttctaa aggagataaa    1320
gagctcagga ctggtaaaga gaaggtcacc tctggtagca caaccaccac gcgtcgttca    1380
tgctctaaaa ccgttactaa gactgttatt ggtcctgatg gtcacaaaga agttaccaaa    1440
gaagtggtga cctccgaaga tggttctgac tgtcccgagg caatggattt aggcacattg    1500
tctggcatag gtactctgga tgggttccgc cataggcacc ctgatgaagc tgccttcttc    1560
gacactgcct caactggaaa aacattccca ggtttcttct cacctatgtt aggagagttt    1620
gtcagtgaga ctgagtctag gggctcagaa tctggcatct tcacaaatac aaaggaatcc    1680
agttctcatc accctgggat agctgaattc ccttcccgtg gtaaatcttc aagttacagc    1740
aaacaattta ctagtagcac gagttacaac agaggagact ccacatttga aagcaagagc    1800
```

```
tataaaatgg cagatgaggc cggaagtgaa gccgatcatg aaggaacaca tagcaccaag    1860
agaggccatg ctaaatctcg ccctgtcaga ggtatccaca cttctccttt ggggaagcct    1920
tccctgtccc cc                                                        1932

<210> SEQ ID NO 2
<211> LENGTH: 1473
<212> TYPE: DNA
<213> ORGANISM: homo sapiens

<400> SEQUENCE: 2
atgaaaagga tggtttcttg gagcttccac aaacttaaaa ccatgaaaca tctattattg      60
ctactattgt gtgttttttct agttaagtcc caaggtgtca acgacaatga ggagggtttc    120
ttcagtgccc gtggtcatcg accccttgac aagaagagag aagaggctcc cagcctgagg    180
cctgccccac cgcccatcag tggaggtggc tatcgggctc gtccagccaa agcagctgcc    240
actcaaaaga aagtagaaag aaaagcccct gatgctggag ctgtcttca cgctgaccca     300 gacctggggg tgttgtgtcc tacaggatgt cagttgcaag aggctttgct acaacaggaa    360
aggccaatca gaatagtgt tgatgagtta ataacaatg tggaagctgt ttcccagacc      420
tcctcttctt cctttcagta catgtatttg ctgaaagacc tgtggcaaaa gaggcagaag    480
caagtaaaag ataatgaaaa tgtagtcaat gagtactcct cagaactgga aaagcaccaa    540
ttatatatag atgagactgt gaatagcaat atcccaacta accttcgtgt gcttcgttca    600
atcctggaaa acctgagaag caaaatacaa agttagaat ctgatgtctc agctcaaatg     660
gaatattgtc gcaccccatg cactgtcagt tgcaatattc ctgtggtgtc tggcaaagaa    720
tgtgaggaaa ttatcaggaa aggaggtgaa acatctgaaa tgtatctcat tcaacctgac    780
agttctgtca aaccgtatag agtatactgt gacatgaata cagaaaatgg aggatgggaca   840 gtgattcaga accgtcaaga cggtagtgtt gactttggca ggaaatggga tccatataaa    900 cagggattg gaaatgttgc aaccaacaca gatgggaaga attactgtgg cctaccaggt     960
gaatattggc ttggaaatga taaaattagc cagcttacca ggatgggacc cacagaactt   1020
ttgatagaaa tggaggactg gaaaggagac aaagtaaagg ctcactatgg aggattcact   1080
gtacagaatg aagccaacaa ataccagatc tcagtgaaca atacagagg aacagccggt    1140 aatgccctca tggatggagc atctcagctg atgggagaaa acaggaccat gaccattcac   1200
aacggcatgt tcttcagcac gtatgacaga gacaatgacg gctggttaac atcagatccc   1260
agaaaacagt gttctaaaga agacggtggt ggatggtggt ataatagatg tcatgcagcc   1320
aatccaaacg gcagatacta ctggggtgga cagtacacct gggacatggc aaagcatggc   1380
acagatgatg gtgtagtatg gatgaattgg aagggtcat ggtactcaat gaggaagatg    1440
agtatgaaga tcaggccctt cttcccacag caa                                1473

<210> SEQ ID NO 3
<211> LENGTH: 1311
<212> TYPE: DNA
<213> ORGANISM: Homo sapiens

<400> SEQUENCE: 3
atgagttggt ccttgcaccc ccggaattta attctctact ctatgctct tttatttctc      60 tcttcaacat gtgtagcata tgttgctacc agagacaact gctgcatctt agatgaaaga    120
ttcggtagtt attgtccaac tacctgtggc attgcagatt tcctgtctac ttatcaaacc    180
aaagtagaca aggatctaca gtctttggaa gacatcttac atcaagttga aaacaaaaca    240
```

```
tcagaagtca aacagctgat aaaagcaatc caactcactt ataatcctga tgaatcatca      300
aaaccaaata tgatagacgc tgctactttg aagtccagga aatgttaga agaaattatg      360 aaatatgaag catcgatttt aacacatgac tcaagtattc gatatttgca ggaaatatat      420
aattcaaata atcaaaagat tgttaacctg aaagagaagg tagcccagct tgaagcacag      480
tgccaggaac cttgcaaaga cacggtgcaa atccatgata tcactgggaa agattgtcaa      540
gacattgcca ataagggagc taaacagagc gggctttact ttattaaacc tctgaaagct      600
aaccagcaat tcttagtcta ctgtgaaatc gatgggtctg aaatggatg gactgtgttt       660 cagaagagac ttgatggcag tgtagatttc aagaaaaact ggattcaata taagaagga      720 tttggacatc tgtctcctac tggcacaaca gaattttggc tgggaaatga aagattcat     780 ttgataagca cacagtctgc catcccatat gcattaagag tggaactgga agactggaat      840
ggcagaacca gtactgcaga ctatgccatg ttcaaggtgg acctgaagc tgacaagtac      900 cgcctaacat atgcctactt cgctggtggg gatgctggag atgcctttga tggctttgat     960
tttggcgatg atcctagtga caagttttc acatcccata atggcatgca gttcagtacc      1020
tgggacaatg acaatgataa gtttgaaggc aactgtgctg aacaggatgg atctggttgg      1080
tggatgaaca gtgtcacgc tggccatctc aatggagttt attaccaagg tggcacttac      1140
tcaaaagcat ctactcctaa tggttatgat aatggcatta tttgggccac ttggaaaacc      1200
cggtggtatt ccatgaagaa aaccactatg aagataatcc cattcaacag actcacaatt      1260
ggagaaggac agcaacacca cctgggggga gccaaacagg ctggagacgt t               1311
```

<210> SEQ ID NO 4
<211> LENGTH: 1932
<212> TYPE: DNA
<213> ORGANISM: Homo sapiens

<400> SEQUENCE: 4

```
atgttcagca tgaggatcgt gtgcctggtg ctgtccgtgg tgggcaccgc ctggaccgcc       60
gacagcggcg agggcgactt cctggccgag ggcggtggcg tgaggggccc cagggtggtg      120
gagaggcacc agagcgcctg caaggacagc gactggccct tctgcagcga cgaggactgg      180
aactacaagt gccccagcgg ctgcaggatg aagggcctga tcgacgaggt gaaccaggac      240
ttcaccaaca ggatcaacaa gctgaagaac agcctgttcg agtaccagaa gaacaacaag      300
gacagccaca gcctgaccac caacatcatg gaaatcctga gggcgatttt ctctagcgcc     360
aacaacaggg acaacaccta aacagggtgt ccgaggacc tgaggtccag gatcgaggtg      420
ctgaagagga aggtgatcga gaaggtgcag cacatccagc tgctgcagaa gaacgtcagg      480
gcccagctgg tcgacatgaa gaggctggaa gtggacatcg acatcaagat caggtcctgc      540
aggggcagct gcagccgggc tctggctaga gaggtggacc tgaaggacta cgaggaccag      600
cagaaacagc tggaacaggt gatcgccaag gacctgctgc ccagcaggga caggcagcac      660
ctgcccctga tcaagatgaa gcccgtgccc gacctggtgc ccggcaactt caagagccag      720
ctgcagaaag tgcccccga gtggaaggcc ctgaccgaca tgccccagat gaggatggaa      780
ctggaaaggc caggcggcaa cgagatcacc agggcggca gcaccagcta cggcaccggc      840
agcgagaccg agagcccag gaaccccag agcgccggca gctggaactc cggcagcagc      900
ggcccaggct ccaccggcaa caggaacccc ggctccagcg gcaccggcgg cacagccacc      960
tggaagcccg gcagctccgg ccctggcagc accggctctt ggaacagcgg cagctctggc     1020
```

```
accgggagca caggcaacca gaacccaggc agccccaggc ctggctctac cgggacctgg   1080
aacccaggct cctccgagag gggctctgcc ggccactgga ccagcgagag cagcgtgagc   1140
ggcagcacag gccagtggca cagcgagtcc ggcagcttca ggcccgacag ccccggcagc   1200
ggcaacgcca ggcccaacaa ccccgactgg ggcaccttcg aggaagtgag cggcaacgtg   1260
agccccggca ccaggcggga gtaccacacc gagaagctgg tgaccagcaa gggcgacaaa   1320
gagctgagga ccggcaaaga aaaggtgacc agcggctcta ccaccaccac caggcggagc   1380
tgcagcaaga ccgtgaccaa gacagtgatc ggccccgacg ccacaaaga ggtgaccaaa   1440 gaagtcgtga ccagcgagga cggcagcgac tgccccgagg ccatggacct gggcacctg   1500 agcggcatcg gcaccctgga cggcttcagg cacaggcacc ccgacgaggc cgccttcttc   1560
gacaccgcca gcaccggcaa gaccttcccc ggcttcttca gccccatgct gggcgagttc   1620
gtgtccgaga ccgagtcccg cggctccgag agcggcatct tcacaaacac caaagagagc   1680 agcaggccacc accccggcat cgccgagttc cccagcaggg gcaagagcag ctcctacagc   1740
aagcagttca ccagcagcac ctcctacaac agaggcgact ccaccttcga gagcaagagc   1800
tacaagatgg ccgacgaggc tggcagcgag gccgaccacg agggcaccca cagcaccaag   1860
aggggccacg ccaagagcag gcccgtgagg ggcatccaca ccagcccct gggcaagccc   1920 agcctgagcc cc                                                       1932

<210> SEQ ID NO 5
<211> LENGTH: 1473
<212> TYPE: DNA
<213> ORGANISM: Homo sapiens

<400> SEQUENCE: 5
atgaagagga tggtgtcctg gtccttccac aagctgaaaa caatgaagca cctgctcctc     60
ctcctcctct gcgtgttcct ggtgaagagc cagggcgtga acgacaacga agagggcttc    120
ttcagcgcca gaggacaccg ccccctggac aagaagagag aagaggcccc cagcctgaga    180
cccgccccac ccccaatcag cggcggaggg tacagagcca ggcccgccaa ggctgccgcc    240
acccagaaga aggtcgaacg gaaggctccc gacgccggag gatgcctgca cgccgacccc    300
gacctgggcg tgctgtgccc caccggctgc cagctgcagg aagctctgct ccagcaggaa    360
aggcccatca gaaacagcgt ggacgagctg aacaacaacg tggaggccgt gagccagacc    420
agcagcagca gcttccagta catgtacctg ctgaaggacc tgtggcagaa gaggcagaag    480
caggtcaaag acaacgagaa cgtggtgaac gagtacagca gcgagctgga gaagcaccag    540
ctgtacatcg acgagaccgt gaacagcaat atcccaacca acctgagggt gctgagaagc    600
atcctggaga acctgaggtc caagatccag aagctggaga gcgacgtcag cgcccagatg    660
gagtactgca ggaccccctg caccgtgtcc tgcaacatcc cagtggtgtc cggcaaggaa    720
tgcgaggaaa tcatcaggaa gggcggcgag accagcgaga tgtacctgat ccagcccgac    780
agcagcgtga agccctacag ggtgtactgc gacatgaaca ccgagaatgg gggctggacc    840
gtcatccaga caggcagga cggcagcgtg gacttcggca ggaagtggga cccctacaag    900
cagggcttcg gcaacgtggc caccaacacc gacggcaaga actactgcgg cctgcctggc    960
gagtattggc tgggaaacga caagatcagc cagctgacca ggatgggccc aaccgagctg   1020
ctgatcgaga tggaggactg gaagggcgac aaggtgaaag cccactacgg cggcttcacc   1080
gtgcagaacg aggccaacaa gtaccagatc agcgtgaaca gtacagggg caccgccggc   1140 aacgccctga tggacggcgc ctcccagctg atgggcgaga acaggaccat gaccatccac   1200
```

```
aacggcatgt tcttcagcac ctacgacagg gacaacgacg gctggctgac cagcgacccc    1260
agaaagcagt gcagcaagga agatggcgga ggatggtggt acaacaggtg ccacgccgcc    1320 aacccccaacg gcaggtacta ctggggcgga cagtacacct gggacatggc caagcacggc    1380
accgacgacg gcgtggtgtg gatgaactgg aaggggtcct ggtacagcat gaggaagatg    1440
agcatgaaga tcaggccatt ctttccacag cag                                 1473
```

<210> SEQ ID NO 6
<211> LENGTH: 1311
<212> TYPE: DNA
<213> ORGANISM: Homo sapiens

<400> SEQUENCE: 6

```
atgagctggt ccctgcaccc caggaacctg atcctgtact tctacgccct gctgttcctg      60
agcagcacat gcgtcgccta tgtggctacc agggacaact gctgcatcct ggacgagagg     120
ttcggcagct actgccccac cacctgcggc atcgccgact ttctgagcac ctaccagacc     180
aaggtggaca aggacctgca gagcctggag gacatcctgc accaggtgga gaacaagacc     240
agcgaggtga agcagctgat caaggccatc cagctgacct acaaccccga cgagagcagc     300
aagcccaaca tgatcgacgc cgccaccctg aagagcagga gatgctggga ggaaatcatg     360
aagtacgagg ccagcatcct gacccacgac agcagcatca gatacctgca ggaaatctac     420
aacagcaaca accagaagat cgtcaacctg aaggaaaagg tcgcccagct ggaagcccag     480
tgccaggaac cctgcaagga caccgtgcag atccacgaca tcaccggcaa ggactgccag     540
gacatcgcca acaagggcgc caagcagagc ggcctgtact catcaagcc cctgaaggcc      600 aaccagcagt tcctggtgta ctgcgagatc gacggcagcg gcaacggctg gaccgtgttc     660
cagaagaggc tggacggcag cgtggacttc aagaagaact ggattcagta caaggaaggc     720
ttcggccacc tgagccccac cggcaccacc gagttctggc tgggcaacga gaagatccac     780
ctgatcagca cccagagcgc catcccatac gccctgaggg tggagctgga ggactggaac     840
ggcaggacca gcaccgccga ctacgccatg ttcaaagtgg acccgaggc cgacaagtac      900 aggctgacct acgcctactt tgccggaggg gacgctggcg acgccttcga cggcttcgac     960
ttcggcgacg accccagcga caagttcttc accagccaca acggcatgca gttcagcacc    1020
tgggacaaca caacgacaa gttcgagggc aactgcgccg agcaggacgg ctccgggtgg     1080
tggatgaaca agtgccacgc cgggcacctg aacggcgtgt actaccaggg cggcacctac    1140
agcaaggcca gcacccccaa cggctacgac aacggcatca tctgggccac ctggaaaacc    1200
aggtggtaca gcatgaaaaa aaccaccatg aagatcatcc cattcaacag actgaccatc    1260
ggcgagggcc agcagcacca cctgggcgga gccaagcagg ctggcgacgt g            1311
```

<210> SEQ ID NO 7
<211> LENGTH: 2598
<212> TYPE: DNA
<213> ORGANISM: Homo sapiens

<400> SEQUENCE: 7

```
atgttcagca tgaggatcgt gtgcctggtg ctgtccgtgg tgggcaccgc ctggaccgcc      60
gacagcggcg agggcgactt cctggccgag ggcggtggcg tgaggggccc cagggtggtg     120
gagaggcacc agagcgcctg caaggacagc gactggccct tctgcagcga cgaggactgg     180
aactacaagt gccccagcgg ctgcaggatg aagggcctga tcgacgaggt gaaccaggac     240
```

```
ttcaccaaca ggatcaacaa gctgaagaac agcctgttcg agtaccagaa gaacaacaag    300
gacagccaca gcctgaccac caacatcatg gaaatcctga ggggcgattt ctctagcgcc    360
aacaacaggg acaacaccta acagggtg tccgaggacc tgaggtccag gatcgaggtg     420
ctgaagagga aggtgatcga aaggtgcag cacatccagc tgctgcagaa aacgtcagg     480 gcccagctgg tcgacatgaa gaggctggaa gtggacatcg acatcaagat caggtcctgc    540
aggggcagct gcagccgggc tctggctaga gaggtggacc tgaaggacta cgaggaccag    600
cagaaacagc tggaacaggt gatcgccaag gacctgctgc ccagcaggga caggcagcac    660 ctgccctga tcaagatgaa gcccgtgccc gacctggtgc ccggcaactt caagagccag    720
ctgcagaaag tgcccccga gtggaaggcc ctgaccgaca tgccccagat gaggatggaa     780
ctggaaaggc caggcggcaa cgagatcacc aggggcggca gcaccagcta cggcaccggc    840
agcgagaccg agagcccag gaaccccagc agcgccggca gctggaactc cggcagcagc    900
ggcccaggct ccaccggcaa caggaacccc ggctccagcg caccggcgg cacagccacc    960 tggaagcccg gcagctccgg ccctggcagc accggctctt ggaacagcgg cagctctggc   1020
accgggagca caggcaacca gaacccaggc agccccaggc ctggctctac cgggacctgg   1080
aacccaggct cctccgagag gggctctgcc ggccactgga ccagcgagag cagcgtgagc   1140
ggcagcacag ccagtggca cagcgagtcc ggcagcttca ggcccgacag ccccggcagc   1200
ggcaacgcca ggcccaacaa ccccgactgg ggcaccttcg aggaagtgag cggcaacgtg   1260
agccccggca ccaggcggga gtaccacacc gagaagctgg tgaccagcaa gggcgacaaa   1320
gagctgagga ccggcaaaga aaggtgacc agcggctcta ccaccaccac caggcggagc   1380
tgcagcaaga ccgtgaccaa gacagtgatc ggccccgacg ccacaaaga ggtgaccaaa   1440 gaagtcgtga ccagcgagga cggcagcgac tgccccgagg ccatggacct gggcaccctg   1500
agcggcatcg gcaccctgga cggcttcagg cacaggcacc ccgacgaggc cgccttcttc   1560
gacaccgcca gcaccggcaa gaccttcccc ggcttcttca gccccatgct gggcgagttc   1620
gtgtccgaga ccgagtcccg cggcagcgag agcggcatct tcaccaacac caaagagtcc   1680
agcagccacc atcccggcat cgctgagttc cccagcaggg gcaagagcag ctcctacagc   1740
aagcagttca ccagcagcac cagctacaac aggggcgaca gcaccttcga gagcaagagc   1800
tacaagatgg ccgacgaggc cggctctgag gccgaccacg agggcaccca cagcaccaag   1860
aggggccacg ccaagagcag gcccgtgagg gactgcgacg acgtgctgca gacccacccc   1920
agcggcaccc agtctggcat cttcaacatc aagctgcccg gcagcagcaa gatcttcagc   1980
gtgtactgcg accaggaaac cagcctgggc ggctggctgc tgatccagca ggaggatggac   2040 ggcagcctga acttcaacag gacctggcag gactacaaga ggggcttcgg ctccctgaac   2100
gacgagggcg agggcgagtt ctggctgggc aacgactacc tgcacctgct gacccagagg   2160
ggatctgtcc tgagggtcga gctggaagat tgggccggca cgaggccta cgccgagtac   2220 cacttcagag tgggcagcga ggccgaggc tacgctctgc aggtgtccag ctacgagggc   2280
acagccggcg acgccctgat cgagggcagc gtggaagagg cgccgagta caccagccac   2340 aacaacatgc agttctccac cttcgacagg gacgccgacc agtgggagga aaactgcgcc   2400
gaggtgtacg gcgagggtg tggtacaac aactgccagg ccgccaacct gaacggcatc   2460
tactacccag gcggcagcta cgaccccagg aacaacagcc cctacagat cgagaacggc   2520 gtggtgtggg tgtccttcag aggcgccgac tacagcctga gggccgtgag gatgaagatc   2580 aggccccctgg tgacccag                                                 2598
```

<210> SEQ ID NO 8
<211> LENGTH: 644
<212> TYPE: PRT
<213> ORGANISM: Homo sapiens

<400> SEQUENCE: 8

Met Phe Ser Met Arg Ile Val Cys Leu Val Leu Ser Val Val Gly Thr
1               5                   10                  15

Ala Trp Thr Ala Asp Ser Gly Glu Gly Asp Phe Leu Ala Glu Gly Gly
            20                  25                  30

Gly Val Arg Gly Pro Arg Val Val Glu Arg His Gln Ser Ala Cys Lys
        35                  40                  45

Asp Ser Asp Trp Pro Phe Cys Ser Asp Glu Asp Trp Asn Tyr Lys Cys
    50                  55                  60

Pro Ser Gly Cys Arg Met Lys Gly Leu Ile Asp Glu Val Asn Gln Asp
65                  70                  75                  80

Phe Thr Asn Arg Ile Asn Lys Leu Lys Asn Ser Leu Phe Glu Tyr Gln
                85                  90                  95

Lys Asn Asn Lys Asp Ser His Ser Leu Thr Thr Asn Ile Met Glu Ile
            100                 105                 110

Leu Arg Gly Asp Phe Ser Ser Ala Asn Asn Arg Asp Asn Thr Tyr Asn
        115                 120                 125

Arg Val Ser Glu Asp Leu Arg Ser Arg Ile Glu Val Leu Lys Arg Lys
    130                 135                 140

Val Ile Glu Lys Val Gln His Ile Gln Leu Leu Gln Lys Asn Val Arg
145                 150                 155                 160

Ala Gln Leu Val Asp Met Lys Arg Leu Glu Val Asp Ile Asp Ile Lys
                165                 170                 175

Ile Arg Ser Cys Arg Gly Ser Cys Ser Arg Ala Leu Ala Arg Glu Val
            180                 185                 190

Asp Leu Lys Asp Tyr Glu Asp Gln Gln Lys Gln Leu Glu Gln Val Ile
        195                 200                 205

Ala Lys Asp Leu Leu Pro Ser Arg Asp Arg Gln His Leu Pro Leu Ile
    210                 215                 220

Lys Met Lys Pro Val Pro Asp Leu Val Pro Gly Asn Phe Lys Ser Gln
225                 230                 235                 240

Leu Gln Lys Val Pro Pro Glu Trp Lys Ala Leu Thr Asp Met Pro Gln
                245                 250                 255

Met Arg Met Glu Leu Glu Arg Pro Gly Gly Asn Glu Ile Thr Arg Gly
            260                 265                 270

Gly Ser Thr Ser Tyr Gly Thr Gly Ser Glu Thr Glu Ser Pro Arg Asn
        275                 280                 285

Pro Ser Ser Ala Gly Ser Trp Asn Ser Gly Ser Ser Gly Pro Gly Ser
    290                 295                 300

Thr Gly Asn Arg Asn Pro Gly Ser Ser Gly Thr Gly Gly Thr Ala Thr
305                 310                 315                 320

Trp Lys Pro Gly Ser Ser Gly Pro Gly Ser Thr Gly Ser Trp Asn Ser
                325                 330                 335

Gly Ser Ser Gly Thr Gly Ser Thr Gly Asn Gln Asn Pro Gly Ser Pro
            340                 345                 350

Arg Pro Gly Ser Thr Gly Thr Trp Asn Pro Gly Ser Ser Glu Arg Gly
        355                 360                 365

Ser Ala Gly His Trp Thr Ser Glu Ser Ser Val Ser Gly Ser Thr Gly

```
              370             375                 380
Gln Trp His Ser Glu Ser Gly Ser Phe Arg Pro Asp Ser Pro Gly Ser
385                 390                 395                 400

Gly Asn Ala Arg Pro Asn Asn Pro Asp Trp Gly Thr Phe Glu Glu Val
                405                 410                 415

Ser Gly Asn Val Ser Pro Gly Thr Arg Arg Glu Tyr His Thr Glu Lys
            420                 425                 430

Leu Val Thr Ser Lys Gly Asp Lys Glu Leu Arg Thr Gly Lys Glu Lys
                435                 440                 445

Val Thr Ser Gly Ser Thr Thr Thr Arg Arg Ser Cys Ser Lys Thr
465                 470                 475                 480

Val Thr Lys Thr Val Ile Gly Pro Asp Gly His Lys Glu Val Thr Lys
465                 470                 475                 480

Glu Val Val Thr Ser Glu Asp Gly Ser Asp Cys Pro Glu Ala Met Asp
                485                 490                 495

Leu Gly Thr Leu Ser Gly Ile Gly Thr Leu Asp Gly Phe Arg His Arg
                500                 505                 510

His Pro Asp Glu Ala Ala Phe Phe Asp Thr Ala Ser Thr Gly Lys Thr
                515                 520                 525

Phe Pro Gly Phe Phe Ser Pro Met Leu Gly Glu Phe Val Ser Glu Thr
                530                 535                 540

Glu Ser Arg Gly Ser Glu Ser Gly Ile Phe Thr Asn Thr Lys Glu Ser
545                 550                 555                 560

Ser Ser His His Pro Gly Ile Ala Glu Phe Pro Ser Arg Gly Lys Ser
                565                 570                 575

Ser Ser Tyr Ser Lys Gln Phe Thr Ser Ser Thr Ser Tyr Asn Arg Gly
                580                 585                 590

Asp Ser Thr Phe Glu Ser Lys Ser Tyr Lys Met Ala Asp Glu Ala Gly
                595                 600                 605

Ser Glu Ala Asp His Glu Gly Thr His Ser Thr Lys Arg Gly His Ala
                610                 615                 620

Lys Ser Arg Pro Val Arg Gly Ile His Thr Ser Pro Leu Gly Lys Pro
625                 630                 635                 640

Ser Leu Ser Pro

<210> SEQ ID NO 9
<211> LENGTH: 491
<212> TYPE: PRT
<213> ORGANISM: Homo sapiens

<400> SEQUENCE: 9

Met Lys Arg Met Val Ser Trp Ser Phe His Lys Leu Lys Thr Met Lys
1               5                   10                  15

His Leu Leu Leu Leu Leu Cys Val Phe Leu Val Lys Ser Gln Gly
            20                  25                  30

Val Asn Asp Asn Glu Glu Gly Phe Phe Ser Ala Arg Gly His Arg Pro
        35                  40                  45

Leu Asp Lys Lys Arg Glu Glu Ala Pro Ser Leu Arg Pro Ala Pro Pro
    50                  55                  60

Pro Ile Ser Gly Gly Gly Tyr Arg Ala Arg Pro Ala Lys Ala Ala Ala
65                  70                  75                  80

Thr Gln Lys Lys Val Glu Arg Lys Ala Pro Asp Ala Gly Gly Cys Leu
                85                  90                  95

His Ala Asp Pro Asp Leu Gly Val Leu Cys Pro Thr Gly Cys Gln Leu
```

100                 105                 110
        Gln Glu Ala Leu Leu Gln Gln Glu Arg Pro Ile Arg Asn Ser Val Asp
                    115                 120                 125

Glu Leu Asn Asn Val Glu Ala Val Ser Gln Thr Ser Ser Ser Ser
            130                 135                 140

Phe Gln Tyr Met Tyr Leu Leu Lys Asp Leu Trp Gln Lys Arg Gln Lys
        145                 150                 155                 160

Gln Val Lys Asp Asn Glu Asn Val Val Asn Glu Tyr Ser Ser Glu Leu
                        165                 170                 175

Glu Lys His Gln Leu Tyr Ile Asp Glu Thr Val Asn Ser Asn Ile Pro
                    180                 185                 190

Thr Asn Leu Arg Val Leu Arg Ser Ile Leu Glu Asn Leu Arg Ser Lys
                    195                 200                 205

Ile Gln Lys Leu Glu Ser Asp Val Ser Ala Gln Met Glu Tyr Cys Arg
                    210                 215                 220

Thr Pro Cys Thr Val Ser Cys Asn Ile Pro Val Val Ser Gly Lys Glu
        225                 230                 235                 240

Cys Glu Glu Ile Ile Arg Lys Gly Gly Glu Thr Ser Glu Met Tyr Leu
                        245                 250                 255

Ile Gln Pro Asp Ser Ser Val Lys Pro Tyr Arg Val Tyr Cys Asp Met
                    260                 265                 270

Asn Thr Glu Asn Gly Gly Trp Thr Val Ile Gln Asn Arg Gln Asp Gly
                    275                 280                 285

Ser Val Asp Phe Gly Arg Lys Trp Asp Pro Tyr Lys Gln Gly Phe Gly
            290                 295                 300

Asn Val Ala Thr Asn Thr Asp Gly Lys Asn Tyr Cys Gly Leu Pro Gly
        305                 310                 315                 320

Glu Tyr Trp Leu Gly Asn Asp Lys Ile Ser Gln Leu Thr Arg Met Gly
                        325                 330                 335

Pro Thr Glu Leu Leu Ile Glu Met Glu Asp Trp Lys Gly Asp Lys Val
                    340                 345                 350

Lys Ala His Tyr Gly Gly Phe Thr Val Gln Asn Glu Ala Asn Lys Tyr
                    355                 360                 365

Gln Ile Ser Val Asn Lys Tyr Arg Gly Thr Ala Gly Asn Ala Leu Met
                    370                 375                 380

Asp Gly Ala Ser Gln Leu Met Gly Glu Asn Arg Thr Met Thr Ile His
        385                 390                 395                 400

Asn Gly Met Phe Phe Ser Thr Tyr Asp Arg Asp Asn Asp Gly Trp Leu
                        405                 410                 415

Thr Ser Asp Pro Arg Lys Gln Cys Ser Lys Glu Asp Gly Gly Gly Trp
                    420                 425                 430

Trp Tyr Asn Arg Cys His Ala Ala Asn Pro Asn Gly Arg Tyr Tyr Trp
                    435                 440                 445

Gly Gly Gln Tyr Thr Trp Asp Met Ala Lys His Gly Thr Asp Asp Gly
                    450                 455                 460

Val Val Trp Met Asn Trp Lys Gly Ser Trp Tyr Ser Met Arg Lys Met
        465                 470                 475                 480

Ser Met Lys Ile Arg Pro Phe Phe Pro Gln Gln
                        485                 490

<210> SEQ ID NO 10
<211> LENGTH: 437
<212> TYPE: PRT
<213> ORGANISM: Homo sapiens

<400> SEQUENCE: 10

```
Met Ser Trp Ser Leu His Pro Arg Asn Leu Ile Leu Tyr Phe Tyr Ala
1               5                   10                  15

Leu Leu Phe Leu Ser Ser Thr Cys Val Ala Tyr Val Ala Thr Arg Asp
            20                  25                  30

Asn Cys Cys Ile Leu Asp Glu Arg Phe Gly Ser Tyr Cys Pro Thr Thr
        35                  40                  45

Cys Gly Ile Ala Asp Phe Leu Ser Thr Tyr Gln Thr Lys Val Asp Lys
    50                  55                  60

Asp Leu Gln Ser Leu Glu Asp Ile Leu His Gln Val Glu Asn Lys Thr
65                  70                  75                  80

Ser Glu Val Lys Gln Leu Ile Lys Ala Ile Gln Leu Thr Tyr Asn Pro
                85                  90                  95

Asp Glu Ser Ser Lys Pro Asn Met Ile Asp Ala Ala Thr Leu Lys Ser
                100                 105                 110

Arg Lys Met Leu Glu Glu Ile Met Lys Tyr Glu Ala Ser Ile Leu Thr
            115                 120                 125

His Asp Ser Ser Ile Arg Tyr Leu Gln Glu Ile Tyr Asn Ser Asn Asn
130                 135                 140

Gln Lys Ile Val Asn Leu Lys Glu Lys Val Ala Gln Leu Glu Ala Gln
145                 150                 155                 160

Cys Gln Glu Pro Cys Lys Asp Thr Val Gln Ile His Asp Ile Thr Gly
                165                 170                 175

Lys Asp Cys Gln Asp Ile Ala Asn Lys Gly Ala Lys Gln Ser Gly Leu
            180                 185                 190

Tyr Phe Ile Lys Pro Leu Lys Ala Asn Gln Gln Phe Leu Val Tyr Cys
            195                 200                 205

Glu Ile Asp Gly Ser Gly Asn Gly Trp Thr Val Phe Gln Lys Arg Leu
210                 215                 220

Asp Gly Ser Val Asp Phe Lys Lys Asn Trp Ile Gln Tyr Lys Glu Gly
225                 230                 235                 240

Phe Gly His Leu Ser Pro Thr Gly Thr Thr Glu Phe Trp Leu Gly Asn
                245                 250                 255

Glu Lys Ile His Leu Ile Ser Thr Gln Ser Ala Ile Pro Tyr Ala Leu
            260                 265                 270

Arg Val Glu Leu Glu Asp Trp Asn Gly Arg Thr Ser Thr Ala Asp Tyr
            275                 280                 285

Ala Met Phe Lys Val Gly Pro Glu Ala Asp Lys Tyr Arg Leu Thr Tyr
290                 295                 300

Ala Tyr Phe Ala Gly Gly Asp Ala Gly Asp Ala Phe Asp Gly Phe Asp
305                 310                 315                 320

Phe Gly Asp Asp Pro Ser Asp Lys Phe Phe Thr Ser His Asn Gly Met
                325                 330                 335

Gln Phe Ser Thr Trp Asp Asn Asp Asn Asp Lys Phe Glu Gly Asn Cys
            340                 345                 350

Ala Glu Gln Asp Gly Ser Gly Trp Trp Met Asn Lys Cys His Ala Gly
            355                 360                 365

His Leu Asn Gly Val Tyr Tyr Gln Gly Gly Thr Tyr Ser Lys Ala Ser
            370                 375                 380

Thr Pro Asn Gly Tyr Asp Asn Gly Ile Ile Trp Ala Thr Trp Lys Thr
385                 390                 395                 400

Arg Trp Tyr Ser Met Lys Lys Thr Thr Met Lys Ile Ile Pro Phe Asn
```

-continued

```
                          405                 410                 415

Arg Leu Thr Ile Gly Glu Gly Gln Gln His Leu Gly Gly Ala Lys
            420                 425                 430

Gln Ala Gly Asp Val
            435

<210> SEQ ID NO 11
<211> LENGTH: 866
<212> TYPE: PRT
<213> ORGANISM: Homo sapiens

<400> SEQUENCE: 11

Met Phe Ser Met Arg Ile Val Cys Leu Val Leu Ser Val Val Gly Thr
1               5                   10                  15

Ala Trp Thr Ala Asp Ser Gly Glu Gly Asp Phe Leu Ala Glu Gly Gly
            20                  25                  30

Gly Val Arg Gly Pro Arg Val Val Glu Arg His Gln Ser Ala Cys Lys
        35                  40                  45

Asp Ser Asp Trp Pro Phe Cys Ser Asp Glu Asp Trp Asn Tyr Lys Cys
    50                  55                  60

Pro Ser Gly Cys Arg Met Lys Gly Leu Ile Asp Glu Val Asn Gln Asp
65                  70                  75                  80

Phe Thr Asn Arg Ile Asn Lys Leu Lys Asn Ser Leu Phe Glu Tyr Gln
                85                  90                  95

Lys Asn Asn Lys Asp Ser His Ser Leu Thr Thr Asn Ile Met Glu Ile
            100                 105                 110

Leu Arg Gly Asp Phe Ser Ser Ala Asn Asn Arg Asp Asn Thr Tyr Asn
        115                 120                 125

Arg Val Ser Glu Asp Leu Arg Ser Arg Ile Glu Val Leu Lys Arg Lys
    130                 135                 140

Val Ile Glu Lys Val Gln His Ile Gln Leu Leu Gln Lys Asn Val Arg
145                 150                 155                 160

Ala Gln Leu Val Asp Met Lys Arg Leu Glu Val Asp Ile Asp Ile Lys
                165                 170                 175

Ile Arg Ser Cys Arg Gly Ser Cys Ser Arg Ala Leu Ala Arg Glu Val
            180                 185                 190

Asp Leu Lys Asp Tyr Glu Asp Gln Gln Lys Gln Leu Glu Gln Val Ile
        195                 200                 205

Ala Lys Asp Leu Leu Pro Ser Arg Asp Arg Gln His Leu Pro Leu Ile
    210                 215                 220

Lys Met Lys Pro Val Pro Asp Leu Val Pro Gly Asn Phe Lys Ser Gln
225                 230                 235                 240

Leu Gln Lys Val Pro Pro Glu Trp Lys Ala Leu Thr Asp Met Pro Gln
                245                 250                 255

Met Arg Met Glu Leu Glu Arg Pro Gly Gly Asn Glu Ile Thr Arg Gly
            260                 265                 270

Gly Ser Thr Ser Tyr Gly Thr Gly Ser Glu Thr Glu Ser Pro Arg Asn
        275                 280                 285

Pro Ser Ser Ala Gly Ser Trp Asn Ser Gly Ser Ser Gly Pro Gly Ser
    290                 295                 300

Thr Gly Asn Arg Asn Pro Gly Ser Ser Gly Thr Gly Gly Thr Ala Thr
305                 310                 315                 320

Trp Lys Pro Gly Ser Ser Gly Pro Gly Ser Thr Gly Ser Trp Asn Ser
                325                 330                 335
```

```
Gly Ser Ser Gly Thr Gly Ser Thr Gly Asn Gln Asn Pro Gly Ser Pro
                340                 345                 350

Arg Pro Gly Ser Thr Gly Thr Trp Asn Pro Gly Ser Ser Glu Arg Gly
            355                 360                 365

Ser Ala Gly His Trp Thr Ser Glu Ser Ser Val Ser Gly Ser Thr Gly
        370                 375                 380

Gln Trp His Ser Glu Ser Gly Ser Phe Arg Pro Asp Ser Pro Gly Ser
385                 390                 395                 400

Gly Asn Ala Arg Pro Asn Asn Pro Asp Trp Gly Thr Phe Glu Glu Val
                405                 410                 415

Ser Gly Asn Val Ser Pro Gly Thr Arg Arg Glu Tyr His Thr Glu Lys
            420                 425                 430

Leu Val Thr Ser Lys Gly Asp Lys Glu Leu Arg Thr Gly Lys Glu Lys
        435                 440                 445

Val Thr Ser Gly Ser Thr Thr Thr Arg Arg Ser Cys Ser Lys Thr
    450                 455                 460

Val Thr Lys Thr Val Ile Gly Pro Asp Gly His Lys Glu Val Thr Lys
465                 470                 475                 480

Glu Val Val Thr Ser Glu Asp Gly Ser Asp Cys Pro Glu Ala Met Asp
                485                 490                 495

Leu Gly Thr Leu Ser Gly Ile Gly Thr Leu Asp Gly Phe Arg His Arg
            500                 505                 510

His Pro Asp Glu Ala Ala Phe Phe Asp Thr Ala Ser Thr Gly Lys Thr
        515                 520                 525

Phe Pro Gly Phe Phe Ser Pro Met Leu Gly Glu Phe Val Ser Glu Thr
    530                 535                 540

Glu Ser Arg Gly Ser Glu Ser Gly Ile Phe Thr Asn Thr Lys Glu Ser
545                 550                 555                 560

Ser Ser His His Pro Gly Ile Ala Glu Phe Pro Ser Arg Gly Lys Ser
                565                 570                 575

Ser Ser Tyr Ser Lys Gln Phe Thr Ser Ser Thr Ser Tyr Asn Arg Gly
            580                 585                 590

Asp Ser Thr Phe Glu Ser Lys Ser Tyr Lys Met Ala Asp Glu Ala Gly
        595                 600                 605

Ser Glu Ala Asp His Glu Gly Thr His Ser Thr Lys Arg Gly His Ala
    610                 615                 620

Lys Ser Arg Pro Val Arg Asp Cys Asp Asp Val Leu Gln Thr His Pro
625                 630                 635                 640

Ser Gly Thr Gln Ser Gly Ile Phe Asn Ile Lys Leu Pro Gly Ser Ser
                645                 650                 655

Lys Ile Phe Ser Val Tyr Cys Asp Gln Glu Thr Ser Leu Gly Gly Trp
            660                 665                 670

Leu Leu Ile Gln Gln Arg Met Asp Gly Ser Leu Asn Phe Asn Arg Thr
        675                 680                 685

Trp Gln Asp Tyr Lys Arg Gly Phe Gly Ser Leu Asn Asp Glu Gly Glu
    690                 695                 700

Gly Glu Phe Trp Leu Gly Asn Asp Tyr Leu His Leu Thr Gln Arg
705                 710                 715                 720

Gly Ser Val Leu Arg Val Glu Leu Glu Asp Trp Ala Gly Asn Glu Ala
                725                 730                 735

Tyr Ala Glu Tyr His Phe Arg Val Gly Ser Glu Ala Glu Gly Tyr Ala
            740                 745                 750

Leu Gln Val Ser Ser Tyr Glu Gly Thr Ala Gly Asp Ala Leu Ile Glu
```

```
             755                 760                 765
Gly Ser Val Glu Glu Gly Ala Glu Tyr Thr Ser His Asn Asn Met Gln
            770                 775                 780

Phe Ser Thr Phe Asp Arg Asp Ala Asp Gln Trp Glu Glu Asn Cys Ala
785                 790                 795                 800

Glu Val Tyr Gly Gly Gly Trp Trp Tyr Asn Asn Cys Gln Ala Ala Asn
                    805                 810                 815

Leu Asn Gly Ile Tyr Tyr Pro Gly Gly Ser Tyr Asp Pro Arg Asn Asn
                820                 825                 830

Ser Pro Tyr Glu Ile Glu Asn Gly Val Val Trp Val Ser Phe Arg Gly
            835                 840                 845

Ala Asp Tyr Ser Leu Arg Ala Val Arg Met Lys Ile Arg Pro Leu Val
        850                 855                 860

Thr Gln
865

<210> SEQ ID NO 12
<211> LENGTH: 1359
<212> TYPE: DNA
<213> ORGANISM: Homo sapiens

<400> SEQUENCE: 12
atgagctggt ccctgcaccc caggaacctg atcctgtact tctacgccct gctgttcctg      60
agcagcacat gcgtcgccta tgtggctacc agggacaact gctgcatcct ggacgagagg     120
ttcggcagct actgccccac cacctgcggc atcgccgact ttctgagcac ctaccagacc     180
aaggtggaca aggacctgca gagcctggag gacatcctgc accaggtgga gaacaagacc     240
agcgaggtga agcagctgat caaggccatc cagctgacct acaaccccga cgagagcagc     300
aagcccaaca tgatcgacgc cgccaccctg aagagcagga gatgctggag gaaatcatg      360 aagtacgagg ccagcatcct gacccacgac agcagcatca gatacctgca ggaaatctac     420
aacagcaaca accagaagat cgtcaacctg aaggaaaagg tcgcccagct ggaagcccag     480
tgccaggaac cctgcaagga caccgtgcag atccacgaca tcaccggcaa ggactgccag     540
gacatcgcca acaagggcgc caagcagagc ggcctgtact tcatcaagcc cctgaaggcc     600
aaccagcagt tcctggtgta ctgcgagatc gacggcagcg gcaacggctg gaccgtgttc     660
cagaagaggc tggacggcag cgtggacttc aagaagaact ggattcagta caaggaaggc     720
ttcggccacc tgagccccac cggcaccacc gagttctggc tgggcaacga aagatccac      780 ctgatcagca cccagagcgc catcccatac gccctgaggg tggagctgga ggactggaac     840
ggcaggacca gcaccgccga ctacgccatg ttcaaagtgg acccgaggc cgacaagtac      900 aggctgacct acgcctactt tgccggaggg gacgctggcg acgccttcga cggcttcgac     960
ttcggcgacg accccagcga caagttcttc accagccaca cggcatgca gttcagcacc     1020 tgggacaacg acaacgacaa gttcgagggc aactgcgccg agcaggacgg ctccgggtgg    1080
tggatgaaca agtgccacgc cgggcacctg aacgcgtgt actaccaggg cggcacctac     1140
agcaaggcca gcacccccaa cggctacgac aacggcatca tctgggccac ctggaaaacc    1200
aggtggtaca gcatgaaaaa aaccaccatg aagatcatcc cattcaacag actgaccatc    1260
ggcgagggcc agcagcacca cctgggcgga gccaagcagg tgcggccaga gcaccccgcc    1320
gagacagagt acgacagcct gtaccccgag gacgacctg                          1359

<210> SEQ ID NO 13
```

```
<211> LENGTH: 453
<212> TYPE: PRT
<213> ORGANISM: Homo sapiens

<400> SEQUENCE: 13

Met Ser Trp Ser Leu His Pro Arg Asn Leu Ile Leu Tyr Phe Tyr Ala
1               5                   10                  15

Leu Leu Phe Leu Ser Ser Thr Cys Val Ala Tyr Val Ala Thr Arg Asp
                20                  25                  30

Asn Cys Cys Ile Leu Asp Glu Arg Phe Gly Ser Tyr Cys Pro Thr Thr
            35                  40                  45

Cys Gly Ile Ala Asp Phe Leu Ser Thr Tyr Gln Thr Lys Val Asp Lys
50                  55                  60

Asp Leu Gln Ser Leu Glu Asp Ile Leu His Gln Val Glu Asn Lys Thr
65                  70                  75                  80

Ser Glu Val Lys Gln Leu Ile Lys Ala Ile Gln Leu Thr Tyr Asn Pro
                85                  90                  95

Asp Glu Ser Ser Lys Pro Asn Met Ile Asp Ala Ala Thr Leu Lys Ser
            100                 105                 110

Arg Lys Met Leu Glu Glu Ile Met Lys Tyr Glu Ala Ser Ile Leu Thr
        115                 120                 125

His Asp Ser Ser Ile Arg Tyr Leu Gln Glu Ile Tyr Asn Ser Asn Asn
130                 135                 140

Gln Lys Ile Val Asn Leu Lys Glu Lys Val Ala Gln Leu Glu Ala Gln
145                 150                 155                 160

Cys Gln Glu Pro Cys Lys Asp Thr Val Gln Ile His Asp Ile Thr Gly
                165                 170                 175

Lys Asp Cys Gln Asp Ile Ala Asn Lys Gly Ala Lys Gln Ser Gly Leu
            180                 185                 190

Tyr Phe Ile Lys Pro Leu Lys Ala Asn Gln Gln Phe Leu Val Tyr Cys
        195                 200                 205

Glu Ile Asp Gly Ser Gly Asn Gly Trp Thr Val Phe Gln Lys Arg Leu
210                 215                 220

Asp Gly Ser Val Asp Phe Lys Lys Asn Trp Ile Gln Tyr Lys Glu Gly
225                 230                 235                 240

Phe Gly His Leu Ser Pro Thr Gly Thr Thr Glu Phe Trp Leu Gly Asn
                245                 250                 255

Glu Lys Ile His Leu Ile Ser Thr Gln Ser Ala Ile Pro Tyr Ala Leu
            260                 265                 270

Arg Val Glu Leu Glu Asp Trp Asn Gly Arg Thr Ser Thr Ala Asp Tyr
        275                 280                 285

Ala Met Phe Lys Val Gly Pro Glu Ala Asp Lys Tyr Arg Leu Thr Tyr
290                 295                 300

Ala Tyr Phe Ala Gly Gly Asp Ala Gly Asp Ala Phe Asp Gly Phe Asp
305                 310                 315                 320

Phe Gly Asp Asp Pro Ser Asp Lys Phe Phe Thr Ser His Asn Gly Met
                325                 330                 335

Gln Phe Ser Thr Trp Asp Asn Asp Asn Asp Lys Phe Glu Gly Asn Cys
            340                 345                 350

Ala Glu Gln Asp Gly Ser Gly Trp Trp Met Asn Lys Cys His Ala Gly
        355                 360                 365

His Leu Asn Gly Val Tyr Tyr Gln Gly Gly Thr Tyr Ser Lys Ala Ser
370                 375                 380

Thr Pro Asn Gly Tyr Asp Asn Gly Ile Ile Trp Ala Thr Trp Lys Thr
```

-continued

```
           385                 390                 395                 400
Arg Trp Tyr Ser Met Lys Lys Thr Thr Met Lys Ile Ile Pro Phe Asn
                405                     410                 415

Arg Leu Thr Ile Gly Glu Gly Gln Gln His His Leu Gly Gly Ala Lys
                420                 425                 430

Gln Val Arg Pro Glu His Pro Ala Glu Thr Glu Tyr Asp Ser Leu Tyr
            435                 440                 445

Pro Glu Asp Asp Leu
        450
```